(12) United States Patent
Rytwo

(10) Patent No.: US 10,273,169 B2
(45) Date of Patent: Apr. 30, 2019

(54) METHOD FOR PRETREATMENT OF WASTEWATER WITH NANOCOMPOSITES AND BRIDGING POLYMERS

(71) Applicant: GAVISH-GALILEE BIO APPLICATIONS LTD., Kiryat Shmona (IL)

(72) Inventor: Giora Rytwo, Sde Nehemia (IL)

(73) Assignee: GAVISH-GALILEE BIO APPLICATIONS, LTD., Kiryat Shmona (IL)

( * ) Notice: Subject to any disclaimer, the term of this patent is extended or adjusted under 35 U.S.C. 154(b) by 238 days.

(21) Appl. No.: 14/912,316

(22) PCT Filed: Aug. 14, 2014

(86) PCT No.: PCT/IL2014/050738
§ 371 (c)(1),
(2) Date: Feb. 16, 2016

(87) PCT Pub. No.: WO2015/022695
PCT Pub. Date: Feb. 19, 2015

(65) Prior Publication Data
US 2016/0207803 A1    Jul. 21, 2016

Related U.S. Application Data

(63) Continuation-in-part of application No. 13/967,644.
(Continued)

(51) Int. Cl.
*C02F 1/28* (2006.01)
*C02F 1/52* (2006.01)
(Continued)

(52) U.S. Cl.
CPC ............ *C02F 1/288* (2013.01); *C02F 1/5236* (2013.01); *C02F 1/56* (2013.01); *B01D 21/01* (2013.01); *C02F 2103/007* (2013.01); *C02F 2103/20* (2013.01); *C02F 2103/22* (2013.01); *C02F 2103/26* (2013.01); *C02F 2103/322* (2013.01);
(Continued)

(58) Field of Classification Search
None
See application file for complete search history.

(56) References Cited

U.S. PATENT DOCUMENTS 3,066,095 A    11/1962    Hronas
5,071,587 A    12/1991    Perman
(Continued)

FOREIGN PATENT DOCUMENTS

EP    1870380 A1    12/2007
WO    2012176190 A1    12/2012

OTHER PUBLICATIONS

Fuzesy. "Potash in Saskatchewan", 1982, pp. 1-50.*
(Continued)

*Primary Examiner* — Clare M Perrin
(74) *Attorney, Agent, or Firm* — Browdy and Neimark, PLLC

(57) ABSTRACT

A method for pretreatment of wastewater or recreational water with substantial reduction of total suspended solids and turbidity in a very short time is provided comprising treatment with nanocomposites and a bridging agent.

16 Claims, 17 Drawing Sheets
(16 of 17 Drawing Sheet(s) Filed in Color)

Related U.S. Application Data

(60) Provisional application No. 61/955,996, filed on Mar. 20, 2014.

(51) Int. Cl.
    *C02F 1/56*     (2006.01)
    *G01N 33/18*     (2006.01)
    *B01D 21/01*     (2006.01)
    *C02F 103/00*     (2006.01)
    *C02F 103/20*     (2006.01)
    *C02F 103/22*     (2006.01)
    *C02F 103/26*     (2006.01)
    *C02F 103/32*     (2006.01)

(52) U.S. Cl.
    CPC .... *C02F 2103/325* (2013.01); *C02F 2305/08* (2013.01); *G01N 33/1826* (2013.01)

(56) References Cited

U.S. PATENT DOCUMENTS

| | | | |
|---|---|---|---|
| 5,433,865 | A | 7/1995 | Laurent |
| 5,543,056 | A | 8/1996 | Murcott |
| 6,132,625 | A | 10/2000 | Moffett |
| 2005/0258103 | A1 | 11/2005 | Cort |
| 2007/0172913 | A1 | 7/2007 | Hughes et al. |
| 2009/0206040 | A1 | 8/2009 | Berg et al. |
| 2010/0213405 | A1 | 8/2010 | Wensloff |
| 2012/0029120 | A1 | 2/2012 | Soane et al. |
| 2012/0061321 | A1 | 3/2012 | Soane et al. |

OTHER PUBLICATIONS

Rytwo G., "The Use of Clay-Polymer Nanocomposites in Wastewater Pretreatment", The Scientific World Journal, pp. 1-7, vol. 2012 (Feb. 2012).

Rytwo G. et al.,"Clarification of olive mill and winery wastewater by means of clay-polymer nanocomposites" Science of the Total Environment, pp. 134-142, vol. 442 (Jan. 2013).

G. Jock Churchman, "Formation of complexes between bentonite and different cationic polyelectrolytes and their use as sorbents for non-ionic and anionic pollutants", Applied Clay Science, pp. 177-189 vol. 21 (Jun. 2002).

Ganigar et al, "Polymer—clay nanocomposites for the removal of trichlorophenol and trinitrophenol from water", Applied Clay Science, pp. 311-316, vol. 49 (Jul. 2010).

S. M. Mousavi et al, "Use of Modified Bentonite for Phenolic Adsorption in Treatment of Olive Oil Mill Wastewater", Iranian Journal of Science & Technology, Transaction B, Engineering, pp. 613-619, vol. 30, No. B5 (Feb. 2006).

Rytwo et al, "Use of CV- and TPP-montmorillonite for the removal of priority pollutants from water"; Applied Clay Science, pp. 182-190, vol. 36 (Apr. 2007).

Rytwo et al, "Organo-sepiolite particles for efficient pretreatment of organic wastewater: Application to winery effluents"; Applied Clay Science, pp. 390-394, vol. 51; pp. 390-394 (Feb. 2011).

Rytwo et al, "Very fast sorbent for organic dyes and pollutants"; Colloid Polym Sci, pp. 817-820, vol. 284(Apr. 2006).

Zadaka et al, "Atrazine removal from water by polycation-clay composites: Effect of dissolved organic matter and ,ximparison to activated carbon" Water Research, pp. 677-683, vol. 43, pp. 677-683 (Feb. 2009).

Total Organic Carbon, "Online Analysis of organic in water", pp. 1-6, Teledyne Analytical Instruments (2015).

Zimmels et al., "Removal of high organic loads from winery wastewater by aquatic plants", Water Environ Res., pp. 806-22, vol. 80, No. 9 (Sep. 2008).

Masi et al., "Winery high organic content wastewater treated by constructed wetlands in Mediterranean climate", Conference Proceedings of the IWA 8thInternational Conference on Wetland Systems for Water Pollution Control, Arusha (TZ), pp. 274-282, vol. 1, pp. 274-282 (Sep. 2002).

Rytwo and Malka, "A pilot plant for the treatment of cowshed effluents" Water & Irrigation,pp. 6-9, vol. 530 (Sep.-Oct. 2013).

Dharmappa et al., "Wastewater characteristics, management and reuse in mining & mineral processing industries", Encyclopedia of Life Support Systems (EOLSS), pp. 1-10, vol. I, (2002).

Aguirre et al.,"Treatment of piggery wastewater in experimental high rate algal ponds", Rev Latinoam Biotecnol Amb Algal, pp. 57-66 , vol. 2, No. 2 (Dec. 2011).

Dipu et al.,"Phytoremediation of Dairy Effluent by Constructed Wetland Technology Using Wetland Macrophytes" pp. 90-100, vol. 4, No. 2 (2010).

Dultz et al."Effects of different organic cations on the electrokinetic surface charge from organo-montmorillonites—consequences for the adsorption properties", DTTG Annual Meeting, pp. 1-9, vol. 11 (Oct. 5-8, 2005.

Gonen et al.,"Using the dual-mode model to describe adsorption of organic pollutants onto an organoclay" Journal of Colloid and Interface Science, pp. 95-101, vol. 299 (Jul. 2006).

Rytwo et al.,"Direct Relationship Between Electrokinetic Surface-charge Measurement of Effluents and Coagulant Type and Dose" Colloids and Interface Science Communications, pp. 27-30, vol. 1 (Aug. 2014).

Salopek et al.,"Measurement and Application of Zeta-Potential", Rudarsko-geoloiko-naftni zbornik, pp. 147-151, vol. 3 (1992).

Homeyer et al."Optimization of the polyelectrolyte dosage for dewatering sewage sludge suspensions by means of a new centrifugation analyser with an optoelectronic sensor" Colloid Polym Sci, pp. 637-645, vol. 277 (Jul. 1999).

\* cited by examiner

Fig. 1A
App. 2 nm
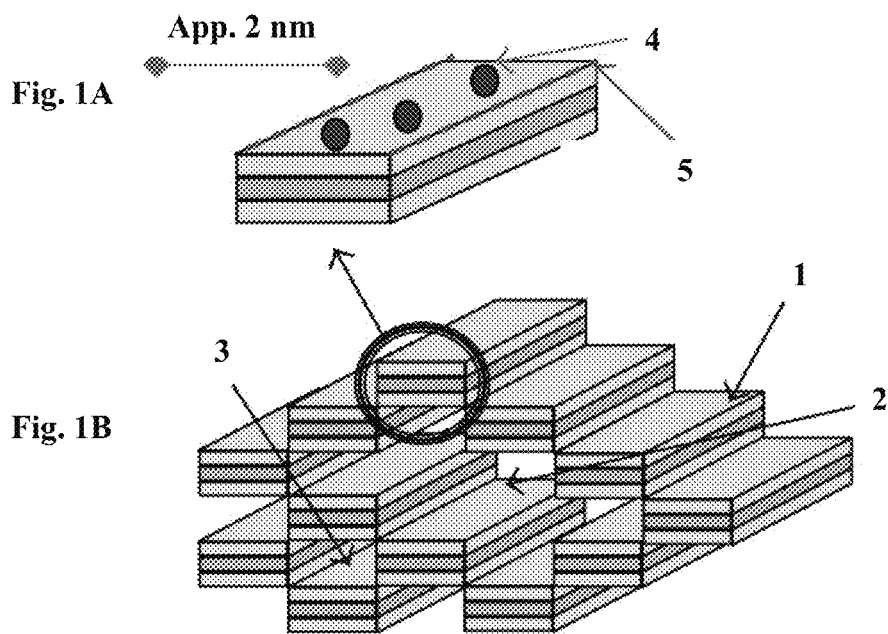
Fig. 1B
Fig. 2
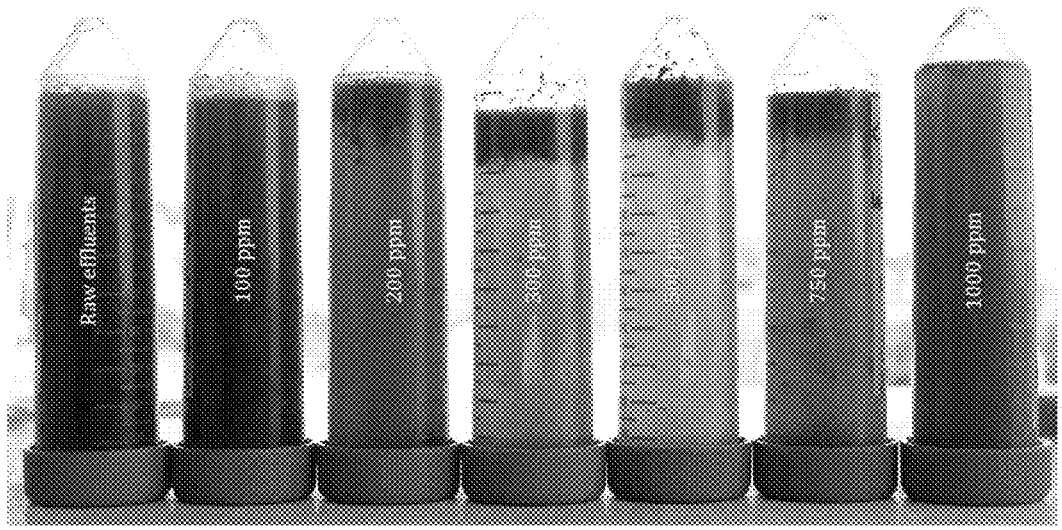

METHOD FOR PRETREATMENT OF WASTEWATER WITH NANOCOMPOSITES AND BRIDGING POLYMERS

FIELD OF THE INVENTION

The present invention relates in general to pretreatment of wastewater or recreational water with a high organic load and, in particular, to such a method using nanocomposites and a bridging agent.

BACKGROUND OF THE INVENTION

There is an urgent need to process specific industrial or agricultural effluents (such as olive mills, wineries, piggeries, soy or coffee bean industries) that are unsuitable for discharge into standard sewage treatment plants due to the large amounts of organic and suspended matter. The disposal of such effluents without any treatment is known to cause serious environmental problems. Wineries are major producers of organically laden wastewater, yielding about 1000-3000 L per ton of grapes characterized by high contents of organic material and nutrients, high acidity, and large variations in seasonal flow production. The very high values of organic matter, suspended solids, and sodium adsorption ratio (SAR) make such water inadequate for disposal in common sewage systems.

Colloidal particles that tend to clog filtering devices are one of the problems with such effluents. In most cases, colloidal stability (i.e., colloids' tendency to remain dispersed) in organically loaded effluents is due to three effects: (a) small particle size, yielding large hydrodynamic friction forces: (b) electrostatic repulsion due to similar charges of the effluent's colloids, which keep the particles in suspension, and (c) the density of the organic colloids, which is close to that of water and, therefore, even if a large neutral particle forms, its sinking velocity will be very slow. In wastewater, colloid removal is crucial to avoiding clogging of aerobic or anaerobic digesters. In several cases, pretreatment processes in wastewater involve use of chemicals for the neutralization, flocculation, and precipitation of those colloids. The first step in this process is a stage technically known as 'coagulation', defined as neutralization of the colloids' charge, thereby reducing electrostatic repulsion between them and enabling their aggregation. In some cases, this process is followed by 'flocculation', in which bridging compounds are used to form chemically bonded links between the neutral colloidal particles, enmeshing them into relatively larger aggregates that, due to their size and density, sink at the bottom of the vessel, leaving a clarified effluent.

Such destabilization of the colloidal suspension, inducing flocculation of large amount of suspended matter, lowers values of total suspended solids (TSS), turbidity, and even the chemical oxygen demand (COD). This, in turn, improves the efficiency of following water treatments, thereby reducing environmental hazard.

Clays and organoclays (clay minerals treated with organocations) have been widely used for the pretreatment of effluents. Combination of clay minerals and organic compounds efficiently removed colloidal solids in paper mill wastewater. Cationic or anionic polyelectrolytes, combinations of coagulants and polyelectrolytes, or even combination of clay minerals and organic quaternary ammonium ions have been used for the removal of organic contaminants from olive mill wastewater. In all cases, considerable changes in the colloidal properties of the effluent, including reduction in turbidity, TSS, COD and other quality parameters were achieved.

U.S. Pat. No. 6,447,686 discloses a high speed coagulant-flocculant and sedimentation method for treating wastewater. The method is based on an arrangement of tanks comprising a mixing tank, an agitating tank, a polymer aggregation tank and a sedimentation tank successively connected, wherein the mixing tank comprises an aggregating agent which is based on clay minerals.

The term "nanoparticle" is usually used for a combined material which has at least on one dimension a size of 100 nm or less. Thus, most clay minerals are considered nanoparticles. The use of clays as building-blocks for assembling organic species at the nanometer range yields useful hybrid nanostructured materials. Nanocomposite materials consisting of polymer molecules and natural or layered minerals like clays can be prepared and designed by the combination of clay minerals with organic polymers interacting at the molecular level (Ruiz-Hitzky, 2001).

In previous studies, we demonstrated the ability of suitable nanoparticles for very efficient removal of phenolic compounds similar to components of olive mill or winery wastewater (Rytwo et al., 2007). Other studies (Rytwo et al., 2011) presented a very effective pretreatment of effluents based on combination of organoclay nanoparticles and crude clay, which changed the colloidal stability of winery and pickle industry effluents, reducing TSS and turbidity for several cycles by means of a two-step process: a first step performed with an organoclay, and a second step performed by adding raw clay. In general, Rytwo et al (2011) process was similar to that used nowadays in the industry: (a) a coagulation step, performed in industry with cationic polymers, or with aluminium sulphate or other inorganic polycations (in Rytwo et al, 2011, the coagulant was based on an organoclay), and (b) a flocculation step performed in the industry with flocculants in several cases based on cationic or anionic polyacrylamide derivatives (in Rytwo et al, 2011, the flocculant was a raw clay mineral).

PCT Publication WO 2012/176190 of the same applicant discloses a one-step method for pretreatment of wastewater or recreational water with a high organic load using nanocomposites consisting of an anchoring particle and a polymer.

SUMMARY OF INVENTION

It has now been found, in accordance with the present invention, that by adding both a nanocomposite and a bridging agent to a wastewater or recreational water with high organic load, large aggregates of the suspended colloidal particles can be obtained leading to their fast sedimentation and enabling easy filtration.

Thus, in one aspect, the present invention relates to a method for pretreatment of wastewater or recreational water with high organic load for fast reduction of total suspended solids (TSS) and turbidity, comprising treatment of said wastewater or recreational water with a nanocomposite and a bridging agent, wherein said nanocomposite consists of anchoring particles and one or more polymers, at least one of said polymers being a polyelectrolyte polymer, and said bridging agent is a polyelectrolyte polymer with low charge density or a nanocomposite consisting of anchoring particles and a polyelectrolyte polymer with low charge density, whereby said polyelectrolyte polymer neutralizes charged colloidal particles suspended in said wastewater or recreational water while anchoring them to the anchoring particles to form small flocs and said bridging agent bridges the small flocs to form large aggregates, thus enhancing their precipitation and achieving a substantial reduction of TSS and turbidity in a very short time.

The anchoring particles of the nanocomposites may be non-clay minerals, diatomaceous earth, powdered activated carbon or clay minerals such as sepiolite, palygorskite, smectite, montmorillonite, vermiculite, hectorite, laponite, bentonite, saponite and the like The polyelectrolyte polymer for use according to the invention can be a polycationic or polyanionic polymer. The bridging agent may be a branched polyelectrolyte polymer with long and slightly charged branches.

In another aspect, the present invention relates to a method for determining the type and dosage of a coagulant suitable for pretreatment of an effluent with high organic load.

BRIEF DESCRIPTION OF THE FIGURES

The patent or application file contains at least one drawing executed in color. Copies of this patent or patent application publication with color drawings will be provided by the Office upon request and payment of the necessary fee.

In the figures and their description below, the following abbreviations are used.

Figure 3:
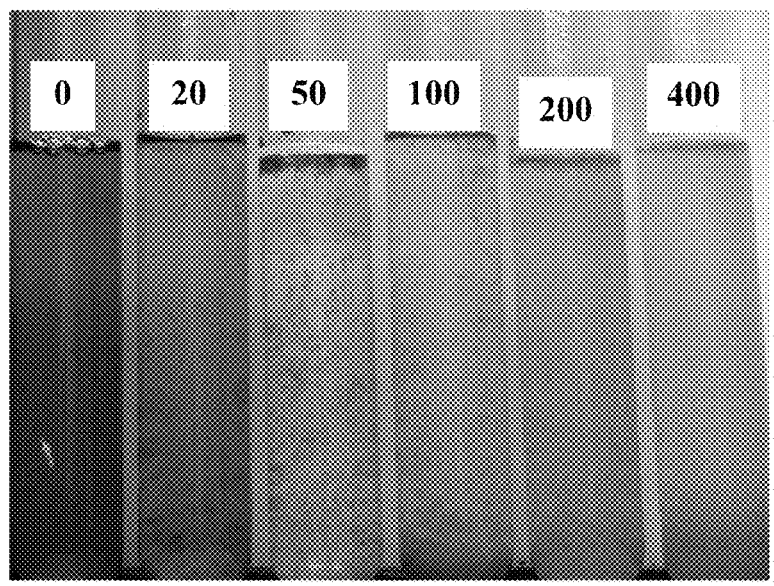

Abbreviations: AM-co-DMAEA, PQ15; BR, PQ15; NC, poly-DADMAC-sepiolite nanocomposite; NCB, nanocomposite suspension based on 30 mg poly-DADMAC per g sepiolite; NC9, nanocomposite suspension based on 40 mg poly-DADMAC per g sepiolite; NC10, nanocomposite suspension based on 60 mg poly-DADMAC per g sepiolite; NC12, nanocomposite suspension based on 100 mg poly-DADMAC per g sepiolite; NC13, nanocomposite suspension based on 120 mg poly-DADMAC per g sepiolite; NC14, nanocomposite suspension based on 160 mg poly-DADMAC per g sepiolite; NC15, nanocomposite suspension based on 200 mg poly-DADMAC per g sepiolite; NC16, nanocomposite suspension based on 240 mg poly-DADMAC per g sepiolite; NC17, nanocomposite suspension based on 320 mg poly-DADMAC per g sepiolite; NC18, nanocomposite suspension based on 400 mg poly-DADMAC per g sepiolite; NC19, NC suspension based on 500 mg poly-DADMAC per g sepiolite; NC21, NC suspension based on 800 mg poly-DADMAC per g sepiolite; NC24, NC suspension based on 1800 mg poly-DADMAC per g sepiolite; NC26, NC suspension based on 2200 mg poly-DADMAC per g sepiolite; NV, poly-DADMAC-bentonite nanocomposite; NH, chitosan-sepiolite nanocomposite; NH6, nanocomposite suspension based on 20 mg chitosan per g sepiolite; NH7, nanocomposite suspension based on 24 mg chitosan per g sepiolite; NH8, nanocomposite suspension based on 30 mg chitosan per g sepiolite; NH9, nanocomposite suspension based on 40 mg chitosan per g sepiolite; NH10, nanocomposite suspension based on 60 mg chitosan per g sepiolite; NH12, nanocomposite suspension based on 100 mg chitosan per g sepiolite; NH13, nanocomposite suspension based on 120 mg chitosan per g sepiolite; NH14, nanocomposite suspension based on 160 mg chitosan per g sepiolite; NH15, nanocomposite suspension based on 200 mg chitosan per g sepiolite; NH18, nanocomposite suspension based on 400 mg chitosan per g sepiolite; NH19, NH suspension based on 500 mg chitosan per g sepiolite; NH21, NH suspension based on 800 mg chitosan per g sepiolite; NZ, AM-co-DMAEA-sepiolite nanocomposite; NZ22, NZ suspension based on 1000 mg AM-co-DMAEA per g sepiolite; OMW, olive oil mill wastewater; PAM, poly(acrylamide-co-acrylic acid) copolymer; PCD, particle charge detector; PD, poly-DADMAC; PD-S9, NC; PDADMAC, poly-DADMAC; PDEE, poly(dimethylamine-co-epichlorohydrin-co-ethylenediamine); PMVE, poly(methyl-vinyl ether-alt-maleic anhydride) copolymer; PMVV, poly[(3-methyl-1-vinylimidazolium chloride)-co-(1-vinylpyrrolidone)]; poly-DADMAC, polyallyl dimethylammonium chloride; PQ, polyquaternium; PQ2, poly[bis(2-chloroethyl)ether-alt-1,3-bis[3-(dimethylamino)-propyl]urea] quaternized; PQ15, acrylamide-dimethylaminoethyl acrylate methyl chloride copolymer; PQ45, methacrylamide, methacrylamido propyl trimonium and methacryloylethyl trimethyl ammonium chloride copolymer; PQ47, terpolymer of acrylic acid, methacrylamidopropyl trimethylammonium chloride, and methyl acrylate; S9, sepiolite; Z, PQ15.

FIGS. 1A-1B depict schematic structures of a single block and connected blocks, respectively, of sepiolite (1), structural defect (2), zeolitic channel (3), charged sites (4), and neutral sites (5). The 2 nm size bar is given as a relative dimension.

FIG. 2 is a picture of tubes with samples of olive mill wastewater (OMW) raw effluents and of OMW treated with increasing amounts (100, 200, 300, 500, 750 and 1000 ppm) of a 2.5% suspension of NC21Z, a coagulant based on nanocomposites comprised of 0.8 g of poly-DADMAC per g sepiolite clay and the bridging agent PQ 15, 10 minutes after the addition of NC21Z (as described in Example 1 herein).

FIG. 3 is a picture of tubes with samples of algae effluents treated with increasing amounts of NC21Z (represented on the tubes as microliter per 50 ml effluents), 10 minutes after the addition of NC21Z (as described in Example 2 herein).

Figure 4:
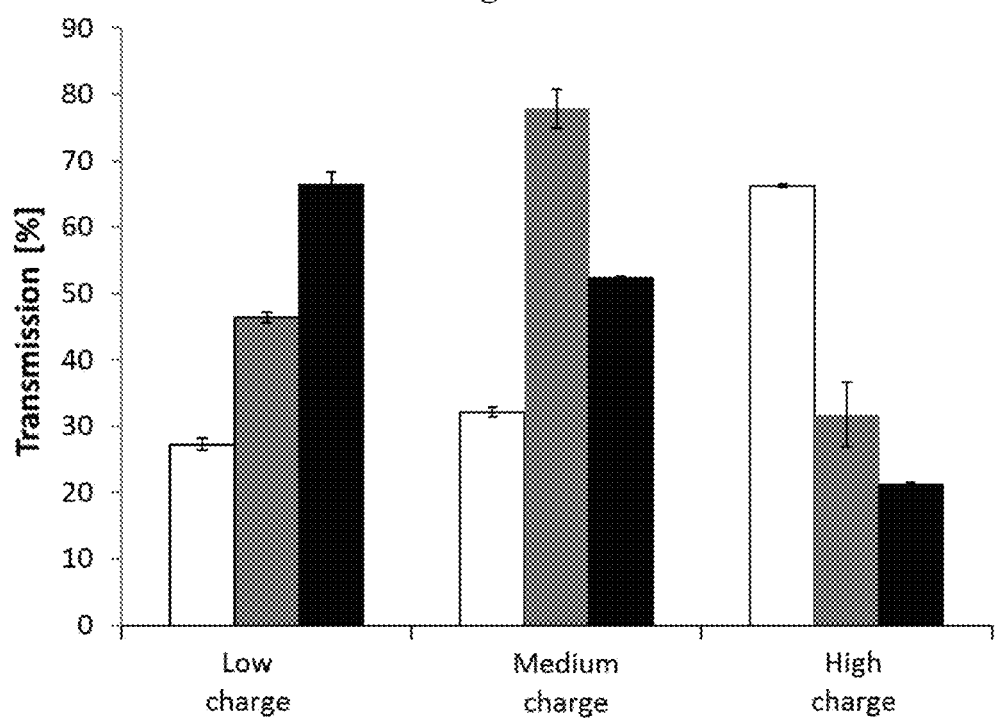

FIG. 4 shows the average light transmission through the upper 90% of test tubes containing highly charged raw OMW as a function of time, after 2 min of centrifugation, treated with 5% suspensions of three different nanocomposite coagulants: (a) low charge (NH21Z=NH21+PQ15, (b) medium charge (NC19Z=NC19+PQ15) and (c) high charge (NC26Z=NC26+PQ15) at doses of 8 (white bars), 40 (gray bars) and 80 (black bars) mL $L^{-1}$ (as described in Example 3 herein).

Figure 5:
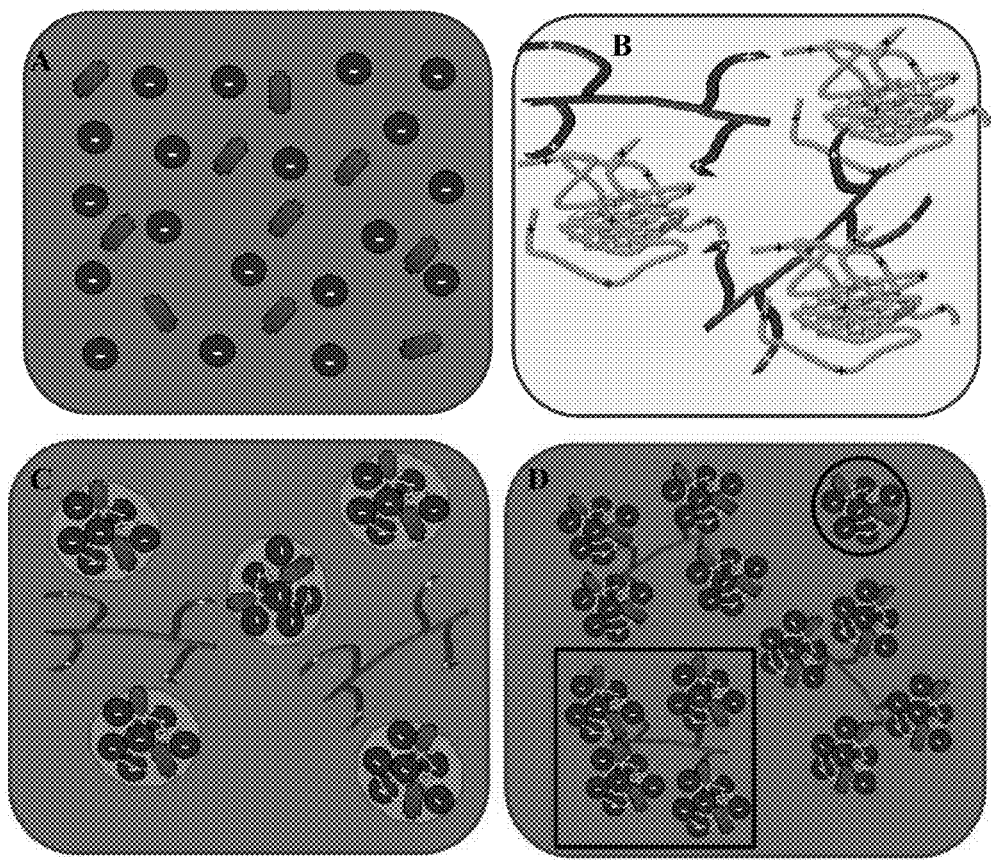

FIG. 5, panels A-D, depict schematic representations of the coagoflocculation method of the invention based on a mixture of a nanocomposite and a bridging agent. A: colloidal particles suspended in an effluent. B: coagoflocculant based on a mixture/combination of a nanocomposite and a bridging agent. C: shows several small flocks formed by the nanocomposites bound to the effluent colloidal particles of A. D: shows several small flocks (marked in a circle) bridged by the bridging agent to form large flocks (marked in a rectangle) that can be easily filtered.

Figure 6:
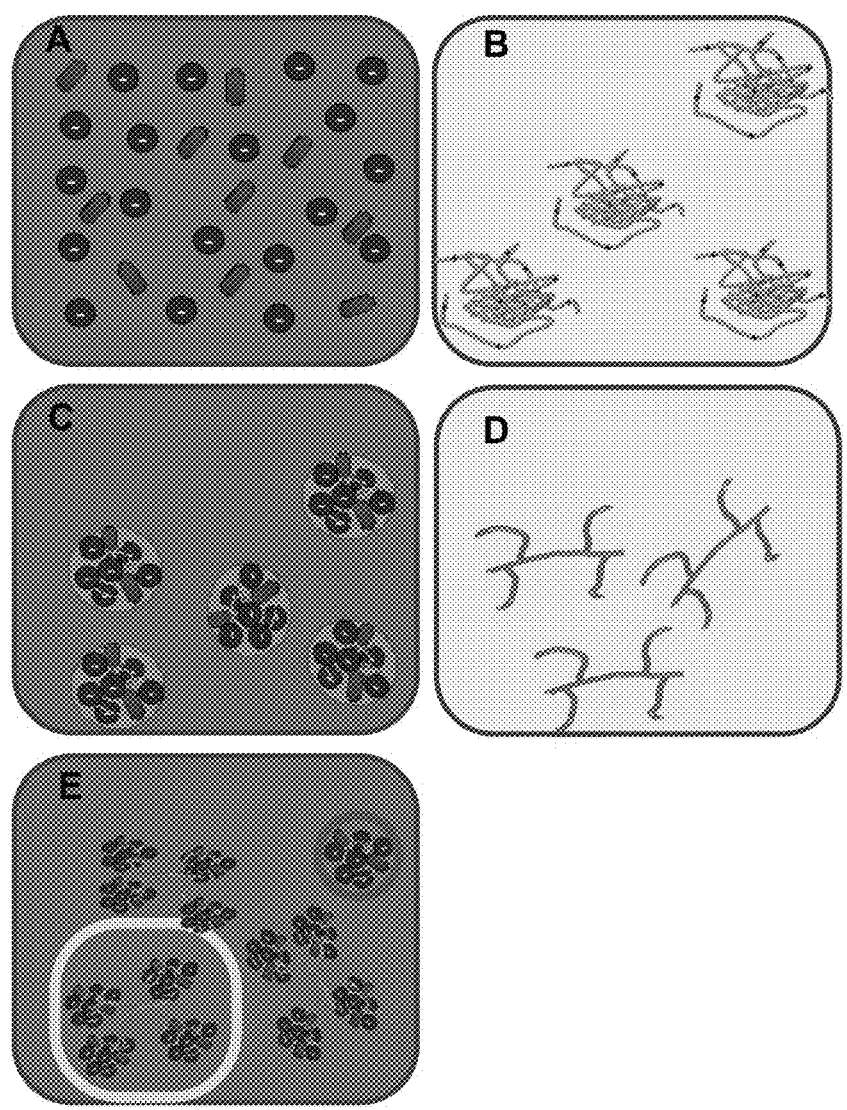

FIG. 6, panels A-E, depict schematic representations of the coagoflocculation method of the invention based on addition of a nanocomposite in excess, followed by addition of a bridging agent having an opposite charge from the nanocomposite charge. A: colloidal particles suspended in an effluent. B: coagoflocculant based on a nanocomposite. C: shows slightly positively charged small flocks formed by the nanocomposites bound to effluent colloidal particles. D: show addition of a bridging agent. Panel E: shows several small flocks (marked in a circle) bridged by the bridging agent to form large flocks (marked in a squircle) that can be easily filtered.

Figure 7:
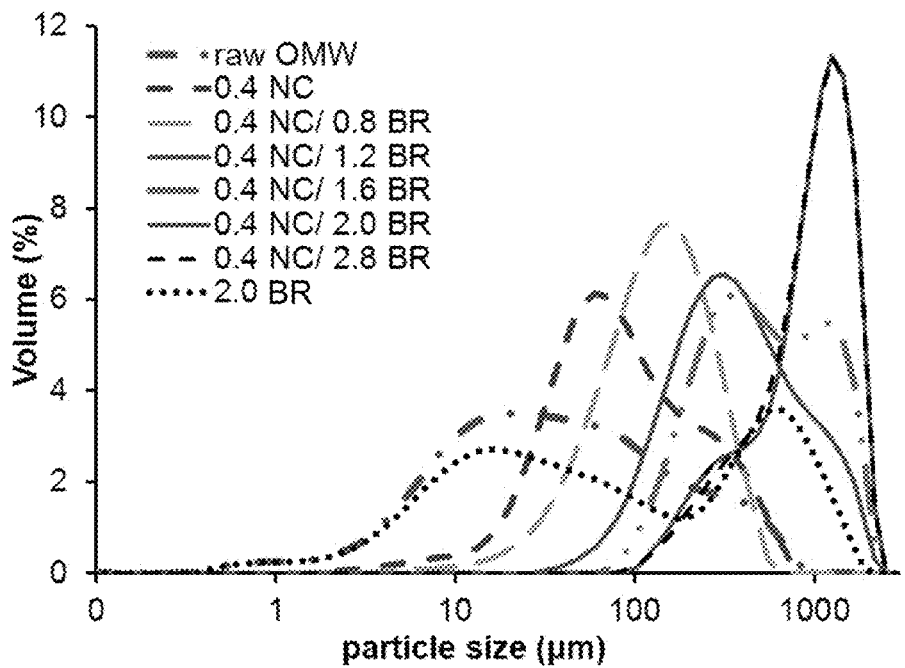

FIG. 7 is a graph showing particle size distribution of colloidal particles of raw OMW effluent (red -•) or of flocks obtained by treatment of OMW effluent treated with 0.4 ml $L^{-1}$ of 5% suspension of the nanocomposite NC26 (NC, --), 2 ml $L^{-1}$ of 2% suspension of the bridging agent PQ15 (BR, gray --), or with a mixture of the nanocomposite (NC; 0.4 ml $L^{-1}$) and the bridging agent (BR) at various amounts (0.5, 1.2, 1.6, 2.0 or 2.8 ml $L^{-1}$) (as described in Example 4 herein).

Figure 8:
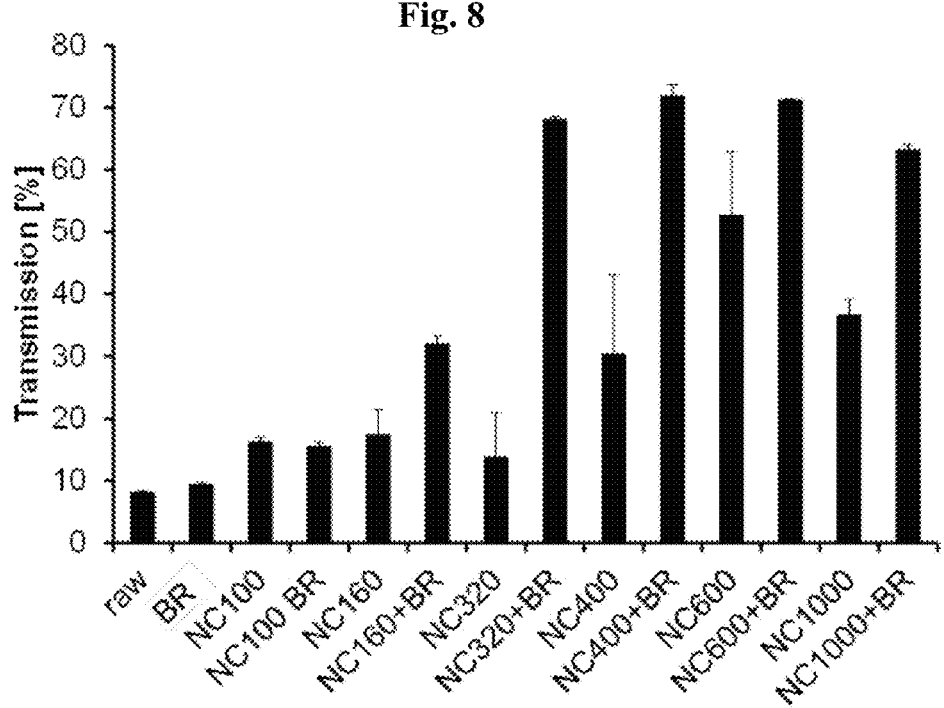

FIG. 8 is a graph showing the light transmission of raw OMW effluent and OMW samples treated with bridging agent PQ15 (BR), with NC nanocomposites of various polymer/clay ratios (NC100, NC160, NC320, NC400, NC600 and NC1000, the numbers represent the amount of poly-DADMAC in mg per g sepiolite) alone or in combination with 15 ml $L^{-1}$ 2% bridging agent PQ 15 (BR) commercial solution. Results were measured 1 min after addition of the coagoflocculant at a relative acceleration force of 5 g (as described in Example 4 herein).

Figure 9:
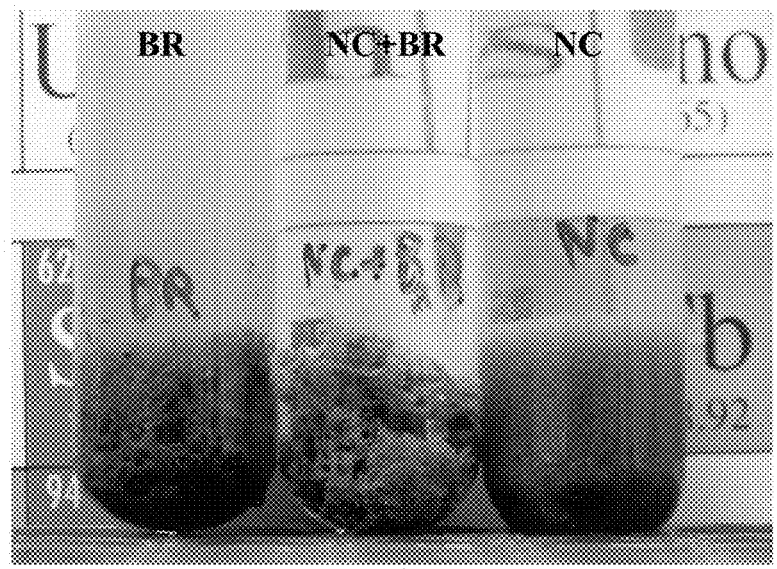

FIG. 9 is a picture of three test tubes with samples of cowshed effluents treated with the bridging agent PQ15 (BR), the nanocomposite NC26 (NC), or with a mixture of both (NC+BR) (as described in Example 5 herein).

Figure 10:
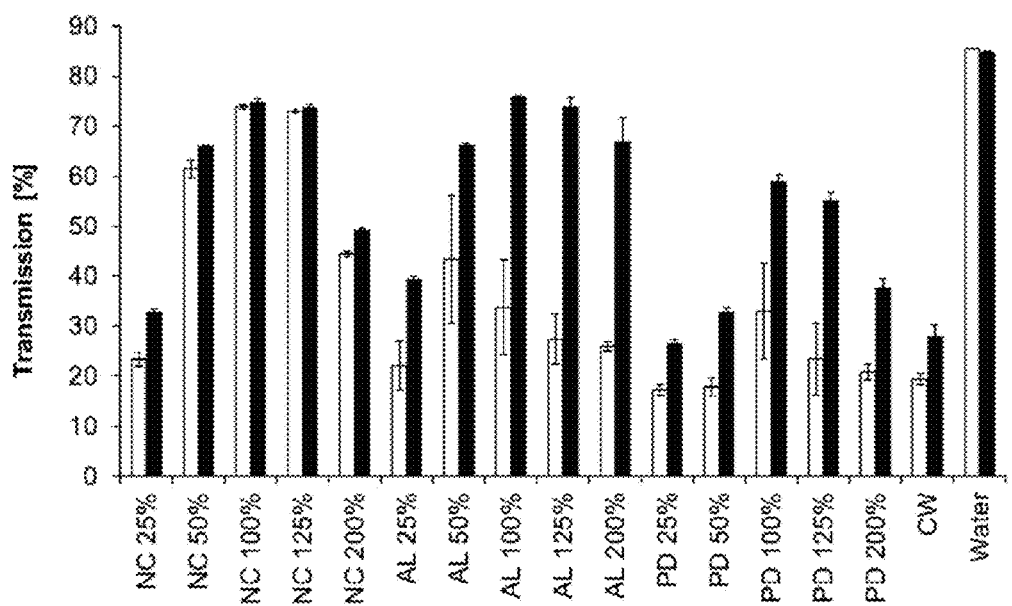

FIG. 10 is a graph showing the light transmission of raw cowshed effluent (CW) or CW effluent treated with NC21Z nanocomposites (NC), aluminum sulfate (AL) or commercial poly-DADMAC (PD) at doses equivalent to 25, 50, 100, 125 and 200% of those required to neutralize the colloids in 10 ml effluents. Results measured with a LUMisizer dispersion analyzer 30 s (white bars) or 150 s (black bars) after addition of the nanocomposite at 200 rpm (equivalent to 5 g centrifugal acceleration) (as described in Example 6 herein).

Figure 11A:
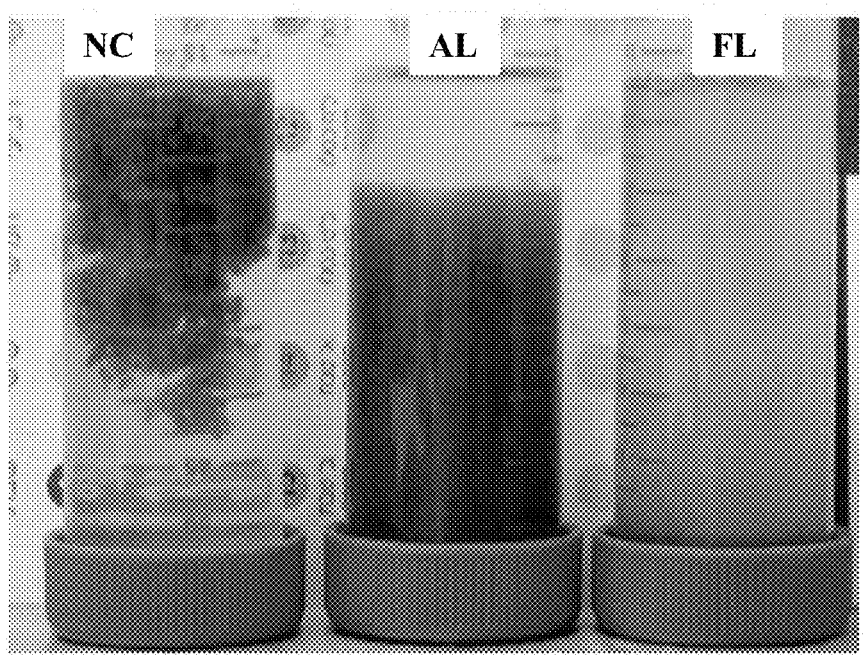
Figure 11B:
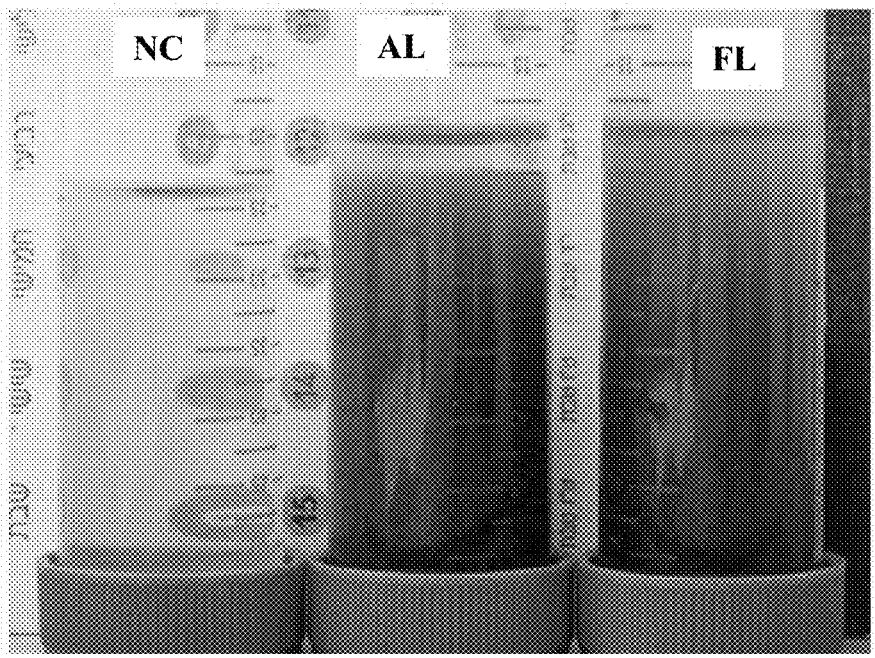

FIGS. 11A-11B are pictures of three test tubes with samples of cowshed effluents treated with NC21Z (NC), aluminum sulfate (AL) or poly-DADMAC (FL), before (11A) and after (11B) filtration through a 212 μm screen (as described in Example 6 herein).

Figure 12:
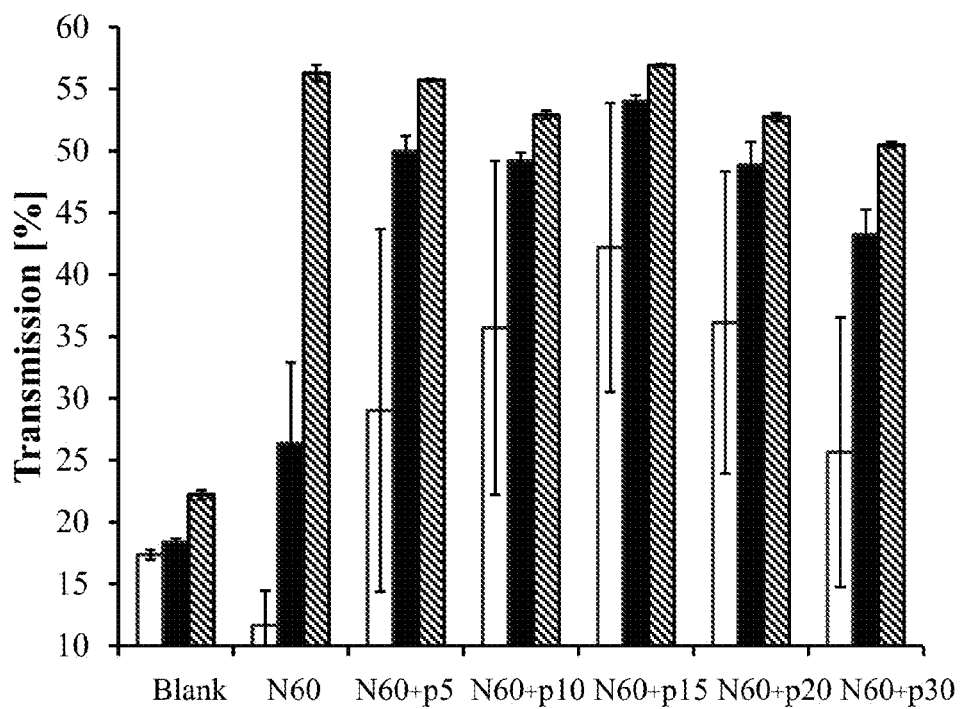

FIG. 12 is a graph showing the light transmission of untreated OMW (Blank) or OMW treated with 5% suspension of NC19 (60 μL of NC19 was added to 10 ml of OMW; N60), or with increasing amounts of a mixture of NC19 and the anionic bridging agent PAM (N60+p5: 60 μL of 5% NC19 and 5 μL of PAM; N60+p10: 60 μL of 5% NC19 and 10 μL of PAM; N60+p15: 60 μL of 5% NC19 and 15 μL of PAM; N60+p20: 60 μL of 5% NC19 and 20 μL of PAM; N60+p30: 60 μL of 5% NC19 and 30 μL of PAM), 1 min (white bars), 2 min (black bars) and 10 min (patterned bars) after centrifugation at 200 RPM (equivalent to a relative centrifugal force of 5 g) (as described in Example 7 herein).

FIGS. 13A-13F are graphs depicting recorded evolution (from left to right) of time dependent transmission profiles of raw OMW sample (Blank, 13A); and of OMW treated with 60 μL of 5% NC19 (N60, 13B); 60 μL of 5% NC19 and 5 μL PAM (N60+p5, 13C), 60 μL of 5% NC19 and 10 μL of PAM (N60+p10, 13D), 60 μL of 5% NC19 and 15 μL of PAM (N60+p15, 13E), and 60 μL of 5% NC19 and 30 μL of PAM (N60+p30, 13F). Profiles were taken every 5 s at a relative centrifugal force of 5 g (200 rpm) for 15 minutes (as described in Example 7 herein).

Figure 14A:
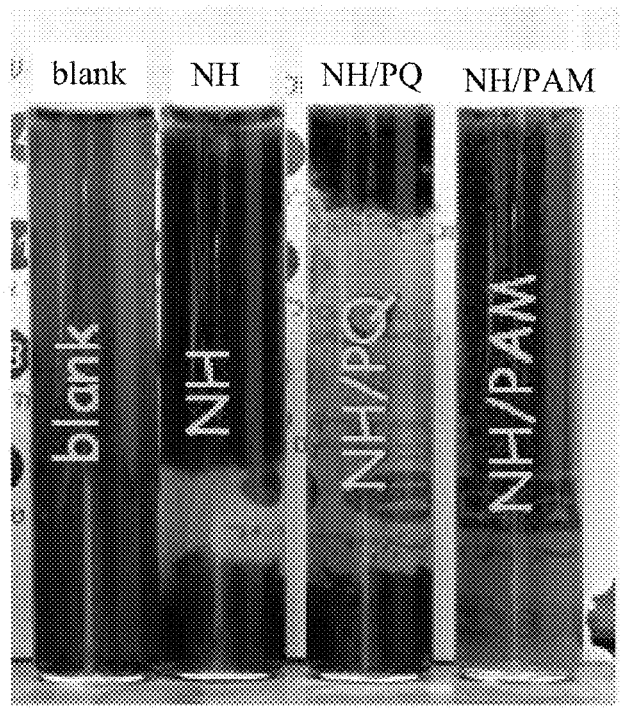
Figure 14B:
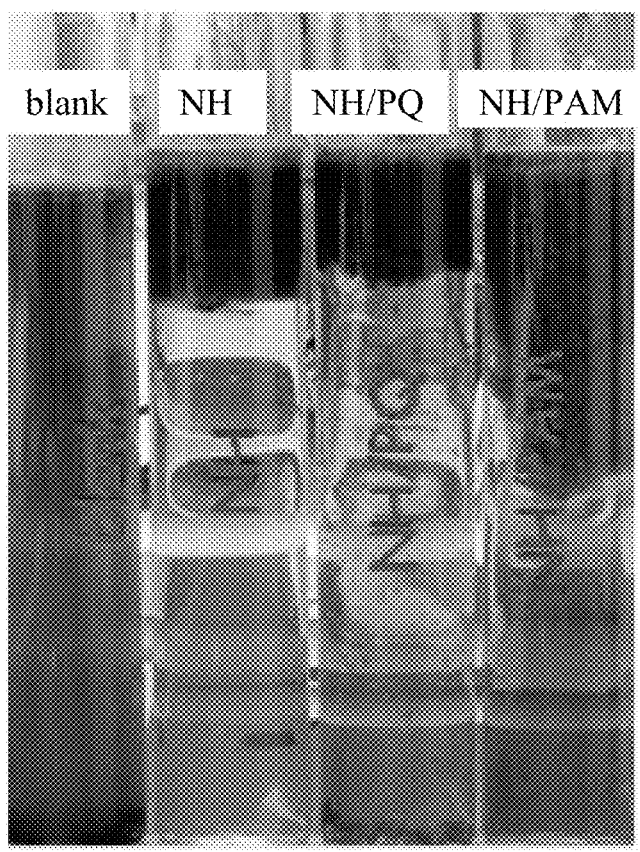

FIGS. 14A-14B are pictures of tubes with samples of raw OMW effluents (blank) or of OMW effluents treated with (i) NH21 nanocomposites (74 μL NH21 per 10 ml effluents, NH), (ii) NH21 and PQ15 (60 μL NH21 and 100 μL of 1% commercial PQ15 per 10 ml effluents, NH/PQ); or (iii) NH21 and PAM (90 μL NH21 per 10 ml effluents, followed by an addition of 15 μL per 10 ml of 10% PAM suspension, NH/PAM). FIGS. 14A-14B are pictures of OMW effluents taken 10 min or 60 min, respectively, after addition of NH, NH/PQ or NH/PAM (as described in Example 8 herein).

Figure 15:
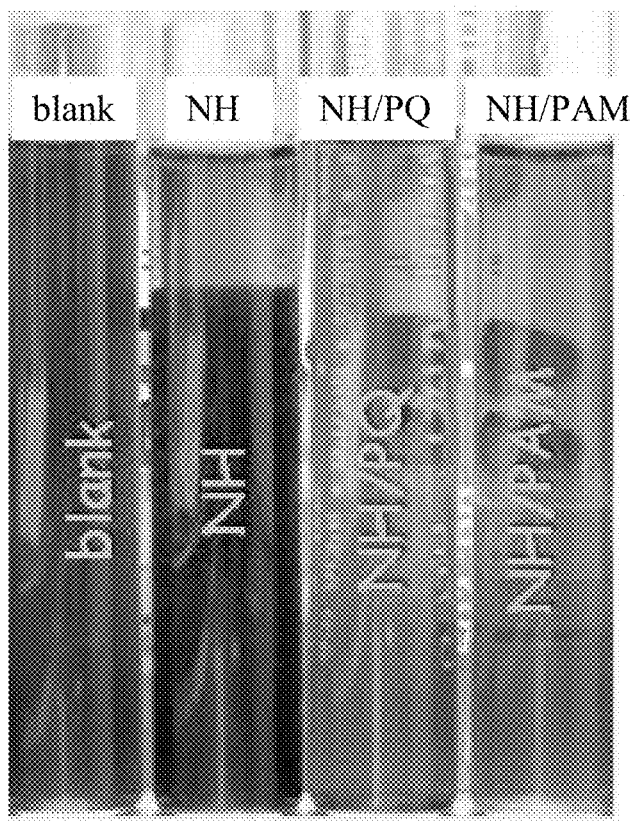

FIG. 15 is a picture of tubes with samples of blank (raw) OMW effluents and OMW effluents treated with NH, NH/PQ or NH/PAM and filtered through a 70 mesh (212 μm) screen (as described in Example 8 herein).

Figure 16:
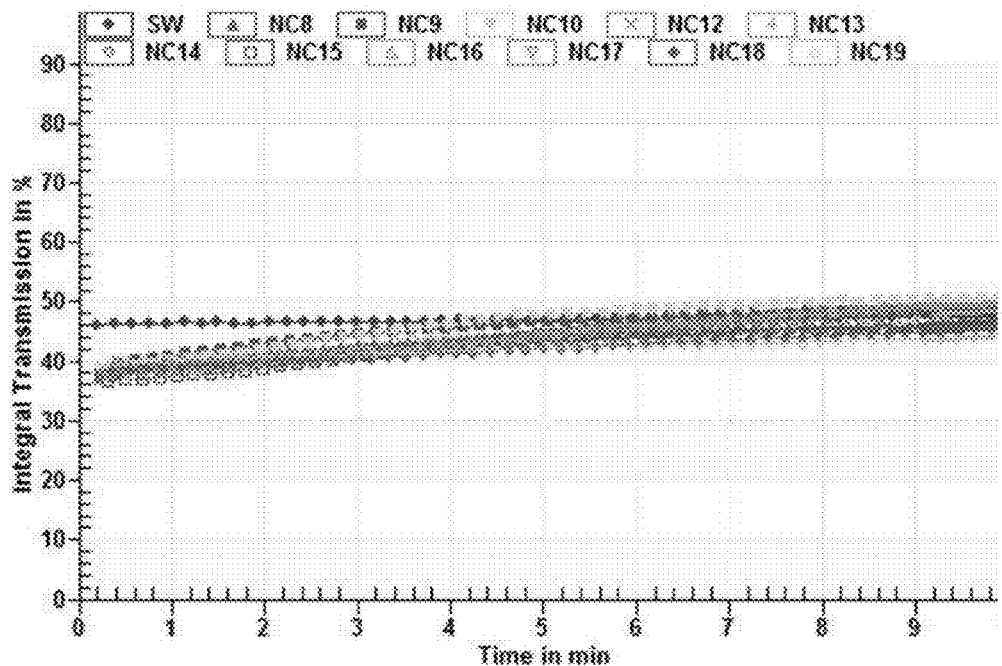

FIG. 16 is a graph showing the light transmission of polluted saline effluents treated with various 5% NC nanocomposites (nanocomposites based on 0.02-0.5 g poly-DADMAC per g sepiolite, denoted as NC8, NC9, NC10, NC12, NC13, NC 14, NC15, NC16, NC17, NC18, and NC19) at the constant dose of 10 ml of NC per L effluent (as described in Example 10 herein).

Figure 17:
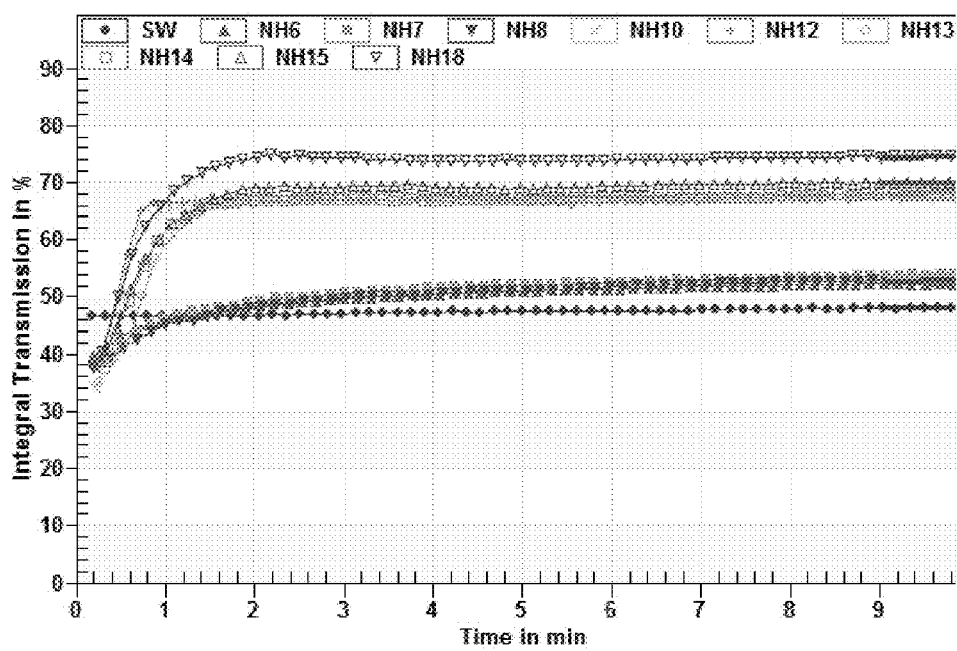

FIG. 17 is a graph showing the light transmission of polluted saline effluents treated with various 5% NH nanocomposites (nanocomposites based on 0.02-0.4 g chitosan per g sepiolite, denoted as NH6, NH7, NH8, NH10, NH12, NH13, NH14, NH15, and NH18) at the constant dose of 10 ml per L effluent (as described in Example 10 herein).

Figure 18:
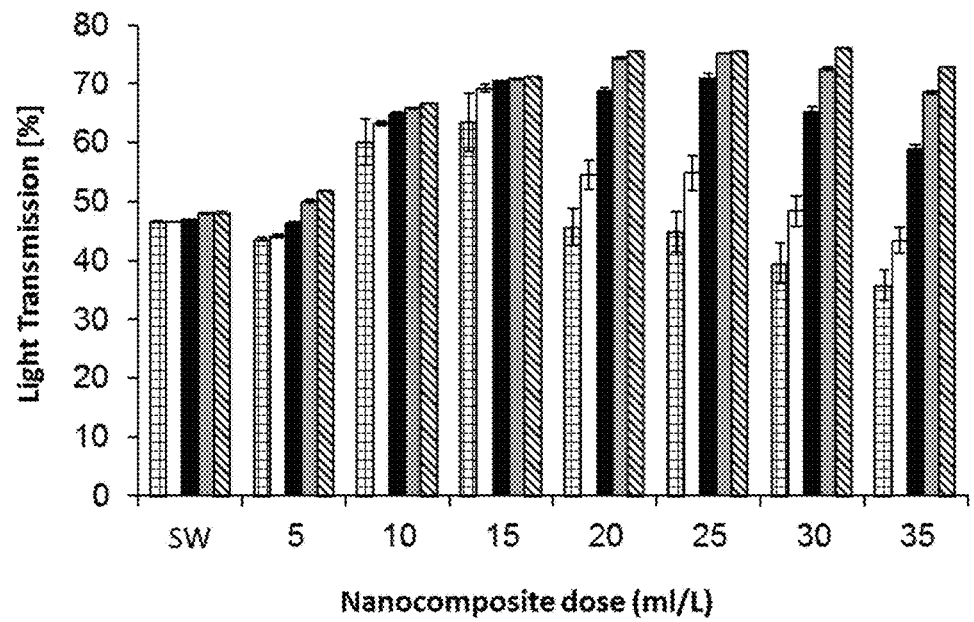

FIG. 18 shows a graph showing the light transmission of saline effluents (SW) and of SW treated with 5, 10, 15, 20, 25, 30 and 35 ml/L of 5% suspension of NH18 nanocomposites, measured 1 min (gridded bars), 2 min (white bars), 5 min (black bars), 10 min (gray bars) and 20 min (hatched bars) (as described in Example 10 herein).

Figure 19:
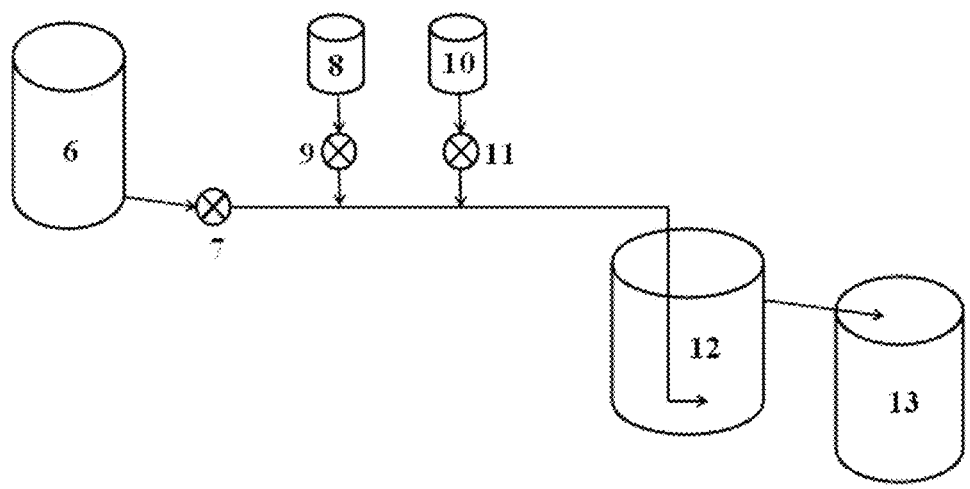

FIG. 19 depicts a continuous system for pretreatment of wastewater with a nanocomposite and a bridging agent. (6), vessel/tank containing the effluent; (7, 9, 11), peristaltic pumps; (8), vessel with nanocomposite suspension; (10), vessel with bridging agent; (12), sedimentation vessel/tank; (13) supernatant vessel/tank (as described in Example 12).

Figure 20A:
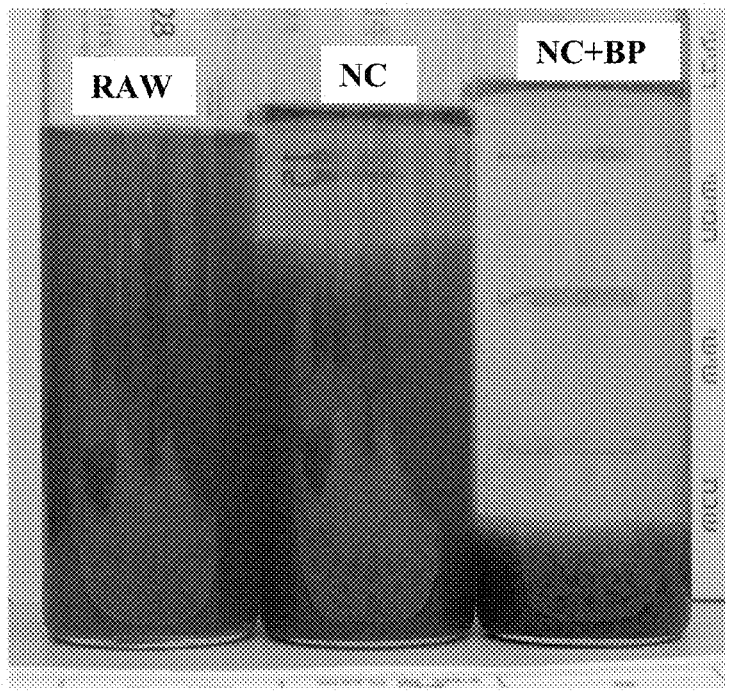
Figure 20B:
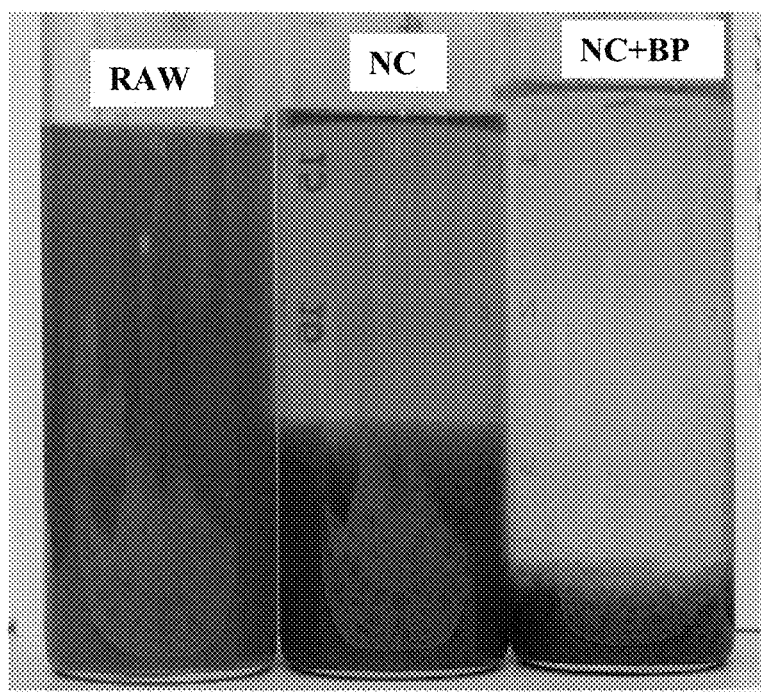

FIGS. 20A-20B are pictures of three test tubes with samples of cowshed effluents taken 10 min or 60 min, respectively, after addition of NC24 (NC) or NC24 and a bridging polymer Zetag®8185 (NC+BP) ((as described in Example 13.2 herein).

FIGS. 21A-21D are pictures of raw cowshed effluent (21A), and of a cowshed effluents treated with NC24 (21B), with NC24 and BP (21C), or with NC24 and NZ22 (21D) (as described in Example 13.4 herein).

DETAILED DESCRIPTION OF THE INVENTION

The present invention is drawn to the use of a combination of a bridging agent and a nanocomposite comprising anchoring particles and one or more polymers, at least one of the polymers being a polyelectrolyte polymer, for efficient and fast reduction of total suspended solids (TSS) and turbidity in highly loaded organic wastewaters such as olive oil mill, wineries, piggeries, cowsheds, dairy effluents, soy or coffee bean industry, etc, in a very short time.

In one aspect, the present invention relates to a method for pretreatment of wastewater or recreational water with high organic load for fast reduction of total suspended solids (TSS) and turbidity, comprising treatment of said wastewater or recreational water with a nanocomposite and a bridging agent, wherein said nanocomposite consists of anchoring particles and one or more polymers, at least one of said polymers being a polyelectrolyte polymer, and said bridging agent is a polyelectrolyte polymer with low charge density or a nanocomposite consisting of anchoring particles and a polyelectrolyte polymer with low charge density, whereby said polyelectrolyte polymer neutralizes charged colloidal particles suspended in said wastewater or recreational water while anchoring them to the anchoring particles to form small flocks and said bridging agent bridges the small flocks to form large aggregates, thus enhancing their precipitation and achieving a substantial reduction of TSS and turbidity in a very short time.

As used herein, the "substantial reduction of TSS" is meant to be of at least two orders of magnitude and the "very short time" is meant to be within the range of seconds to tens of minutes, preferably 0.5 to 10 min, more preferably less than 5 minutes. The method thus achieves a very rapid and efficient pretreatment of the wastewater or recreational water. The terms "wastewater or recreational water" and "effluent" will be used herein interchangeably to refer to the water being pretreated.

A very important feature of the method is the formation of large aggregates. Very small colloidal particles suspended in an effluent have very low sedimentation rates and tend to clog filtering devices. Large aggregates sediment and precipitate enabling their separation from the clear liquid. According to the present method, the addition of the nanocomposites generate small flocks of about 50 to 100 μm size and the addition of the bridging agent bridges the small flocks to generate large aggregates of about 200 to 2000 μm size.

The nanocomposites for use in the method of present invention are composed of anchoring particles and one or more polymers, at least one of which is a polyelectrolyte polymer. The anchoring particles should have the following properties: (i) a size/diameter of less than 0.5 μm in at least one dimension, resulting in a large specific surface area; (ii) the ability to adsorb cationic or anionic polymers in strong interactions; (iii) the bulk density of the particles should be larger than the density of the effluents. According to the invention, the anchoring particles may be based on zeolites, diatomaceous earth, powdered activated carbon or aluminium or magnesium silicate clay minerals. In certain embodiments, the anchoring particles are based on clay minerals selected from sepiolite, palygorskite, smectite, montmorillonite, vermiculite, hectorite, laponite, bentonite, or saponite. In certain embodiments, the clay mineral is sepiolite or bentonite. In certain embodiments, the needle-like clay mineral sepiolite is used as the anchoring particle. Its general structure consists of alternating blocks and tunnels that grow in the direction of the fiber (FIG. 1A). All corners are connected to adjacent blocks (FIG. 1B), but in outer blocks some of the corners form neutral sites accessible to organic molecules. In addition to that, some isomorphic substitutions in the lattice of the mineral form negatively charged adsorption sites. These characteristics of sepiolite make it a powerful sorbent.

In certain embodiments, the nanocomposite consists of the anchoring particles and one, two or three polymers, at least one of which is a polyelectrolyte polymer. In certain embodiments, the nanocomposite consists of anchoring particles and one polymer, which is a polyelectrolyte polymer. In certain embodiments, the polyelectrolyte polymer is a polycationic polymer. In certain other embodiments, the polyelectrolyte polymer is a polyanionic polymer. When the nanocomposite comprises more than one polymer, the additional polymer(s) may be a non-ionic polymer such as, but not limited to, polyethylene glycol, cellulose ether, polyvinyl alcohol, polyvinylpyrrolidone, and copolymers containing aromatic units as styrene, for example, styrene-acrylic acid copolymers.

Any polycationic or polyanionic polymer used in effluent treatment may be considered for use in the present invention. Colloidal stability of the effluents is governed by the size of the particles, their density and their charge. Most organic effluents, such as olive oil mill, wineries, piggeries, cowsheds, slaughterhouses, fruit and vegetable processing industry, or soy or coffee bean industry, recreational water such as a coastal beach or a lake, river or pond, contain colloidal particles with a negative charge, and the polyelectrolyte polymer should have positive charges to neutralize the negative charge of the colloidal particles. In addition, the polyelectrolyte polymer should preferably have medium to long chains with the charges dispersed along/throughout such as to allow the bridging of the neutralized colloidal particles between them while anchoring to the anchoring particles. The polyelectrolyte polymer should also be relatively soluble in water to allow its efficient distribution in the effluents.

Thus, according to certain embodiments the polyelectrolyte polymer is a water-soluble polycationic polymer, with medium to long chain (500-5000 monomers) and charges dispersed along/throughout the polymer.

In certain embodiments, the polycationic polymer is selected from: poly(diallyl dimethylammonium) chloride (poly-DADMAC), cationic polyacrylamide, poly(dimethylamine-co-epichlorohydrin-co-ethylenediamine) (PDEE), poly[bis(2-chloroethyl) ether-alt-1,3-bis[3-(dimethylamino)propyl]urea] quaternized (PQ2), poly [(3-methyl-1-vinylimidazolium chloride)-co-(1-vinylpyrrolidone)] (PMVV), chitosan, poly [(2-ethyldimethylammonioethyl methacrylate ethyl sulfate)-co-(1-vinylpyrrolidone)], quaternized hydroxyethylcellulose ethoxylate, and guar gum. In certain embodiments, the polycationic polymer is poly-DADMAC, PDEE, PQ2 or PMVV chitosan. In certain embodiments, the polyanionic polymer is a poly(methyl vinyl ether-alt-maleic anhydride) copolymer (PMVE) or a poly(acrylamide-co-acrylic acid) copolymer (PAM).

In certain embodiments the nanocomposite for use in the method of the invention consists of anchoring particles based on sepiolite or bentonite and a polycationic or polyanionic polymer. In certain embodiments, the nanocomposite is selected from poly-DADMAC-sepiolite, poly-DADMAC-bentonite, chitosan-sepiolite, PDEE-sepiolite, PQ2-sepiolite, PMVV-sepiolite, PMVE-sepiolite, or PAM-sepiolite. Examples of ranges of quantitative ratios between the mineral clay and the polyelectrolyte include: (i) poly-DADMAC-sepiolite—from 3 to 3000 mg/g, 30 to 2400 mg/g, 80 to 1800 mg/g, or 500 to 1000 mg/g poly-DADMAC to sepiolite; (ii) poly-DADMAC-bentonite—from 3 to 500 mg/g, 30 to 490 mg/g, or 130 to 165 mg/g poly-DADMAC to bentonite; (iii) chitosan-sepiolite—from 3 to 1200 mg/g, 120 to 1000 mg/g, or 500 to 800 mg/g chitosan to sepiolite; (iv) PMVE-sepiolite—from 20 to 500 mg/g, 40 to 320 mg/g, or 60 to 100 mg/g PMVE copolymer to sepiolite; and (v) PAM-sepiolite—from 20 to 500 mg/g, 100 to 400 mg/g, or 200 to 300 mg/g PAM copolymer to sepiolite.

The nanocomposites used in the present invention are identified herein in the Examples and Figures by their abbreviations (see Abbreviations, Brief Description of the Figures), sometimes followed by numerals, which are not quantitative but do indicate qualitatively the amount of the polyelectrolyte polymer in the nanocomposite: the higher the number, the higher the amount of polymer. For example, NC14 contains 160 mg poly-DADMAC per g sepiolite, NC19 contains 500 mg poly-DADMAC per g sepiolite, NC21 contains 800 mg poly-DADMAC per g sepiolite, and NC26 contains 2200 mg poly-DADMAC per g sepiolite.

Some of the nanocomposites have been previously disclosed by the inventor (Rytwo, 2012; Rytwo et al., 2011, 2012, 2013: Rytwo, WO 2012/176190). The nanocomposites PDEE-sepiolite, PQ2-sepiolite, PMVV-sepiolite, PMVE-sepiolite, or PAM-sepiolite are new.

For use as flocculants in wastewater treatment, the right polyelectrolyte should have a low to medium, preferably low, charge density. According to certain embodiments, the bridging agent for use in the present invention is a polyelectrolyte with low charge density, with relatively long branches and relatively separated charges. In certain embodiments, the bridging agent is a polycationic polymer selected from polyquaternium 2 (PQ2) (a polyquaternium with low to medium charge density that is suitable for use both as cationic polymer bound to sepiolite and as the bridging agent), polyquaternium 15 (PQ15), polyquaternium 45 (PQ45), or polyquaternium 47 (PQ47). In certain embodiments, the bridging agent is PQ15. In certain other embodiments, the bridging agent is a polyanionic polymer with low charge density such as poly(acrylamide-co-acrylic acid), acrylamide/sodium acryloyldimethyltaurate copolymer, or acrylamide/sodium acryloyldimethyltaurate/acrylic acid terpolymer.

In certain embodiments, the bridging agent is a nanocomposite consisting of anchoring particles and a low charge density polycationic or polyanionic polymer. In certain embodiments, the anchoring particles are based on sepiolite and the polycationic polymer is PQ15, PQ45 or PQ47, i.e., the nanocomposite is PQ15-sepiolite, PQ45-sepiolite, or PQ47-sepiolite. These nanocomposites are new.

A severe problem in water treatment is the colloidal stability due to rejection between particles with identical charge. Pretreatment of industrial effluents such as olive mill or cowshed dairy wastewater includes therefore the addition of 'coagulants' aimed at neutralizing the colloids and reducing their rejection. The 'coagulant' to be used should have a charge opposite to the effluent's charge: when the effluent is negatively charged, a cationic coagulant should be used; when the effluent is positively charged, an anionic coagulant should be used. In the present invention, the 'coagulant' is the combination of the nanocomposite with the bridging agent.

In accordance with the present invention, complete neutralization of the colloidal effluent can be achieved by selecting the nanocomposite and calculating the dose needed to neutralize a given volume of the effluent by using the method of the invention for determining the type and dosage of a coagulant suitable for pretreatment of a colloidal effluent with high organic load as described hereinafter. In this case, the bridging agent's function will be to bridge the small flocks to large aggregates.

In certain embodiments, complete neutralization is not achieved only by the addition of the nanocomposites and total neutralization of the colloidal particles suspended in the effluent may be achieved in two different ways as schematically shown in FIGS. 5 and 6.

In one embodiment, the effluent is negatively charged, the nanocomposite consisting of anchoring particles and at least one polycationic polymer is added thereto in an amount that causes partial neutralization of the negatively charged colloidal particles and a polycationic bridging agent is added either together with (depicted in FIG. 5, panel B), or after, the addition of the nanocomposite, to complete the neutralization of the particles while bridging the small flocks formed to form large aggregates. In certain embodiments, partial neutralization by the nanocomposite with a polycationic polymer is achieved by adding 40% to 90% of the charged needed to neutralize the colloidal particles and the remaining charged particles are neutralized by the polycationic bridging agent which is added to the wastewater or recreational water either together with, or after, the addition of the nanocomposite.

In another embodiment, effluent is negatively charged, the nanocomposite consisting of anchoring particles and at least one polycationic polymer is added thereto with a total charge that is slightly higher, e.g. 110% of the charge of the colloidal particles suspended in the effluent causing formation of slightly positively charged small flocks (inversion of the effluent's charge), which are neutralized and caused to form large and firm aggregates by later addition (30 sec to 2 min) of a polyanionic bridging agent (schematically shown in FIG. 6). The total treatment time is about less than 5 min.

In certain embodiments, the effluent is positively charged, the nanocomposite consisting of anchoring particles and at least one polyanionic polymer is added thereto in an amount that causes partial neutralization of the positively charged colloidal particles and a polyanionic bridging agent is added either together with, or after, the addition of the nanocomposite, to complete the neutralization of the particles while bridging the small flocks formed to form large aggregates.

In certain other embodiments, the effluent is positively charged, the nanocomposite consisting of anchoring particles and at least one polyanionic polymer is added thereto with a total charge that is slightly higher, e.g. 110% of the charge of the colloidal particles suspended in the wastewater or recreational water causing formation of slightly negatively charged small flocks (inversion of charge), which are neutralized and caused to form large aggregates by later addition of a polycationic bridging agent.

As mentioned above, in order to overcome the severe problem of colloidal stability due to rejection between particles with identical charge, pretreatment of industrial effluents such as olive mill or cowshed dairy wastewater includes the addition of 'coagulants' aimed at neutralizing the colloids and reducing their rejection. However, the amount and type of coagulant are usually determined by "trial-and-error" jar tests due to the a lack of an efficient method to evaluate the effluents' charge. The present invention provides a method for the direct evaluation of the efficiency of various types and doses of coagulants. The procedure aims to simply equalize the charges of the colloidal effluents and that of the added coagulant.

An important feature of the method of the invention is that it can be used in continuous processes. For this purpose, a vessel containing a nanocomposite suspension and another containing the bridging agent are installed in a system for pretreatment of wastewater and the suspensions are pumped into the effluent in the calculated dosages as necessary. In the sedimentation tank, the precipitate is removed and the clarified effluent is transferred to a supernatant vessel for further treatment (FIG. 19).

Thus, in a second aspect, the present invention relates to a method for determining the type and dosage of a coagulant suitable for pretreatment of a colloidal effluent with high organic load, said method comprising the steps:
 (i) measuring the concentration of charges in said effluent;
 (ii) selecting a coagulant of charge opposite to the charge of said effluent and measuring the concentration of charges in said coagulant; and
 (iii) dosing the volume of coagulant needed to neutralize a given volume of the effluent according to the concentration of charges values determined in (i) and (ii).

An electrokinetic technique based on a streaming current detector (SCD), applied in a PCD instrument, is devised to measure the amount of electrokinetic surface charge directly by combining an electrokinetic SCD probe with titration of a charge-compensating polyelectrolyte. The technique is relatively simple and requires no additional model assumptions. The principle of charge measurement is based on the generation of a streaming potential which is induced by the oscillating movement of a plunger in a polytetrafluoroethylene (PTFE) cell, while gold electrodes placed in the cell record the electrokinetic signal. The surface charge is then quantified by titration with charge compensating polyelectrolytes. Addition of the titration solution is performed across the point of zero charge, i.e., the point at which the electrokinetic surface charge measured by the SCD is zero (Dultz and Rytwo, 2005).

In certain embodiments, measurement of the concentration of charges in the method of the invention for determining the type and dosage of a coagulant is performed by polyelectrolyte titration with a particle charge detector (PCD). Thus, in the method above, measurement of charges and calculations are performed as follows:

in step (i), $C_e$, the concentration of charges in the effluent in $mol_e L^{-1}$ is measured by performing polyelectrolyte titration with a particle charge detector (PCD);

in step (ii), the suitable coagulant of charge opposite to the effluent's charge is subjected to PCD measurement yielding $C_c$, the concentration of charges in the coagulant in $mol_c L^{-1}$; and in step (iii), the volume of coagulant (Vc) needed to neutralize a given volume of effluent (Ve) is calculated by the ratios: $V_c/V_e = |C_e/C_c|$.

Implementation of the method above is described in the Examples hereinafter.

In this method, the selection of the coagulant is correlated to the type of charge of the effluent. Thus, when the effluent is negatively charged, a positively charged coagulant is selected, and when the effluent is positively charged, a negatively charged coagulant is selected. In addition, there is also a correlation between the concentration of charge value of the effluent and the charge degree of the selected coagulant. For illustration only, without being bound to these limitations, it can be established that: (a) when the concentration of the negative charge value of the effluent is within the range 0 to −0.5 mmole $L^{-1}$, the coagulant is a low positively charged coagulant; (b) when the concentration of the negative charge value of the effluent is within the range from −1 to −3 mmole $L^{-1}$, the coagulant is a medium positively charged coagulant; (c) when the concentration of the negative charge value of the effluent is within the range from −5 to −9 mmole $L^{-1}$, the coagulant is a highly positively charged coagulant; and (d) when the concentration of the positive charge value of the effluent is within the range from 0.1 to 3 mmole $L^{-1}$, the coagulant is a low or medium negatively charged coagulant.

The coagulant selected by this method can be any coagulant used in pretreatment of effluents, both inorganic coagulants such as aluminum sulfate, aluminum chloride, sodium aluminate, ferric sulfate, ferric chloride, ferric chloride sulfate, hydrated lime and magnesium carbonate, and organic coagulants such as natural or synthetic polymers. The coagulant may also be a nanocomposite as described herein comprised of anchoring particles and one or more polymers, at least one of said polymers being a polyelectrolyte polymer.

The methods of the invention can be applied for pretreatment of a variety of wastewater effluents such as, without being limited to, effluents from olive oil mill, wineries, piggeries, cowsheds, slaughterhouses, fruit and vegetable processing industry, soy or coffee bean industry, bromine industry, dairy effluents, or saline effluents from desalination plants, and for pretreatment of recreational water such as a coastal beach or a lake, river or pond or other water sources containing algae or other particulate material that should be removed, separated or aggregated.

The invention will now be illustrated by the following non-limiting Examples.

EXAMPLES

Materials

Olive mill wastewater (OMW) was kindly supplied by Ein Kamonin Olive Mill (Lower Galilee, Israel). Winery effluents were obtained from Galil Mountain Winery (Yiron, Upper Galilee, Israel). Sepiolite S9 (<200 mesh) was obtained from Tolsa S.A. (Madrid, Spain), with 99% pure mineral content. Poly(diallyldimethylammonium) chloride (poly-DADMAC) medium and high molecular weight 200,000 to 350,000 and 400,000 to 500,000, respectively, and chitosan (medium molecular weight, 75-85% deacetylated) were purchased from Sigma-Aldrich (Israel). Polyquaternium 15, Zetag® 8848FS, Zetag® 8185, ZETAG® 4145 were purchased from BASF, Germany. All materials were used without further treatment or purification.

Methods (a) Analytical Measurements—Electrokinetic Charge Measurements

Electrokinetic charge of the nanocomposite suspensions and the effluents before and after treatment with the nanocomposites (alone or with a bridging agent) were measured by means of a particle charge detector (PCD; Mütek PCD 03) with an automatic titration unit (Mütek titrator T2) using charge-compensating polyelectrolytes as described by Rytwo et al. (2011). Electrokinetic effects occur whenever there is a distortion of counter ions due to movements of charged particles relative to the surrounding solution, and they are widely used to characterize the charge distribution around colloidal particles in an aqueous solution. Results were normalized to $\mu mol_c/g$ (micromoles of charges per gram) of nanocomposite or to $mmol_c/L$ of effluent, accordingly. All experiments were performed in triplicate.

(b) Analytical Measurements—Harmonic mean Sedimentation Velocity

The nanocomposites were tested for their influence on the sedimentation rate of olive oil mill wastewater (OMW). Sedimentation velocities were measured by means of a LUMiSizer (6110) instrument. The instrument records the NIR (near infrared) light transmission during centrifugation over the total length of a cell containing the suspension. It automatically determines the time dependence position of the interface panicle-free fluid/suspension or sediment by a special algorithm. The transmission profile enables characterizing the smallest deviations in size of dispersed particles and quantifying the degree of polydispersity at high-volume concentrations. The harmonic mean sedimentation velocity in the first 60 seconds of the process was chosen as a useful parameter to compare between treatments. High sedimentation velocities were measured when fast precipitation was observed. The reason to focus on the first 60 s is because in the efficient treatments, complete clarification was observed after that period of time. Such experiments allow evaluating the efficiency of the wastewater treatment by a very fast and accurate procedure. Profiles were taken every 5 s for 10 min at a relative centrifugal force of 4.98 g (200 rpm). All experiments were performed three times.

(c) Preparation of Nanocomposites Comprising Sepiolite S9 and Poly-DADMAC (NC Nanocomposites)

NC nanocomposites were prepared from sepiolite and poly-DADMAC at loads ranging between 3 and 2400 mg polymer/g clay. Concentrated batches containing 100 g clay/kg (10%) suspension were prepared. To produce the NC nanocomposites, a solution containing the requested amount of polymer was prepared according to the desired amount of polymer per g of clay. As an example, the procedure for the preparation of a 10% stock suspension of 50 g nanocomposite with 100 mg poly-DADMAC/g sepiolite S9 was as follows. The concentrated polymer (poly-DADMAC, usually 40% w/w) was dissolved in a suitable amount of warm water to obtain a final volume of 500 ml containing 5 g of the polymer. The solution was placed in a sonication bath to obtain a homogeneous solution. Upon complete dissolution, the polymer solution was poured into a container with 50 g of sepiolite and agitated vigorously for 2 hours. Preparation was complete when clay aggregates were no longer observed, and the viscosity of the suspension was relatively low. Increased viscosity indicates that the polymer is not well dissolved or that the process is not yet complete, since a 10% suspension of most clay minerals in water (without polymer) yields a paste that cannot be efficiently used.

(d) Preparation of Nanocomposites Comprising Sepiolite S9 and Chitosan (NH Nanocomposites)

NH nanocomposites were prepared as described in Example 1, but at loads ranging between 3 and 1200 mg polymer/g clay. Concentrated batches containing 50 g clay/kg (5%) suspension were prepared.

(e) Preparation of Nanocomposites Comprising Volclay Sodium Bentonite and Poly-DADMAC (NV Nanocomposites)

NV nanocomposites were prepared as described in Example 1, but at loads ranging between 3 and 500 mg polymer/g clay. Concentrated batches containing 20 g clay/kg (2%) suspension were prepared.

Example 1

Treatment of Olive Oil Mill Wastewater with a Calculated Dosage of Nanocomposite/bridging Agent Suspension OMW pretreated in an anaerobic digester was tested in order to determine the dosage of coagulant. The outflow was very rich in colloidal material (total suspended solids (TSS) =1600 mg $L^{-1}$, turbidity=973 NTU). Coagulation was performed with increasing doses of a 2.5% suspension of NC21Z, a coagulant based on nanocomposites comprised of 0.8 g polyDADMAC (PD) per g sepiolite clay with addition of 10 g/L of polyquaternium 15 (PQ15) bridging agent.

The effluent and coagulant/bridging agent charges were measured by means of a PCD (Mütek PCD 03) with an automatic titration unit (Mütek titrator T2) using charge-compensating polyelectrolytes as described in Method (a) above. Results were normalized to $\mu mol_c/g$ (micromoles of charges per gram) of nanocomposite or to $mmol_c/L$ of effluent, accordingly. TSS concentration was determined by filtering 1-5 ml of the sample trough a 47-mm glass fiber membrane (Sartorius Stedim Biotech GmbH) with a pore diameter of 0.45 µm, and drying at 105° C. for 1 h. Turbidity was measured with a LaMotte 2020i turbidimeter. All experiments were performed in triplicate.

The results are shown in Table 1 and FIG. 2. It can be seen that measuring the charge of the effluents and the charge of the suspension of the nanocomposites/bridging agent coagulant yields a straightforward evaluation of the volume of coagulant to be added in order to achieve efficient clarification. In this case, with an effluent charge of $-1900$ $\mu mol_c$ $L^{-1}$, and a charge of +89000 $\mu mol_c$ $L^{-1}$ for the 2.5% NC21Z suspension, complete neutralization was expected from adding 21 ml of the coagulant suspension per L effluent (equivalent to 533 ppm NC21Z final concentration). Results in Table 1 and FIG. 2 show that, indeed, a final NC21Z concentration of 500 ppm yielded 97% turbidity removal.

TABLE 1

Charge, TSS and turbidity of OMW (initial charge of $-1900$ $\mu mol\ L^{-1}$) treated with increasing amounts of NC21Z 2.5% nanocomposites and PQ15 with an initial charge of +89000 $\mu mol\ L^{-1}$).

| Final concentration of NC21Z [ppm] | Volume of NC21Z suspension added ml $L^{-1}$ | Effluent turbidity after treatment NTU | Measured effluent charge | NC21Z evaluated added charge $\mu mol_c\ L^{-1}$ | Evaluated remaining charge of OMW |
|---|---|---|---|---|---|
| 0 | 0 | 973 | −1900 | 0 | −1900 |
| 100 | 4 | 305 | −1400 | 356 | −1544 |
| 200 | 8 | 146 | −1000 | 712 | −1188 |
| 300 | 12 | 88 | −650 | 1068 | −832 |
| 500 | 20 | 28 | −180 | 1780 | −120 |
| 750 | 30 | 120 | 450 | 2670 | 770 |
| 1000 | 40 | 278 | 1300 | 3560 | 1660 |

FIG. 2 shows that with 300 and 500 ppm coagulant, the effluents are relatively clear and colloids have efficiently aggregated, forming a dense layer of flocks at the top of the tubes.

Example 2

Treatment of an Effluent Containing Algae with a Calculated Dosage of Nanocomposite/bridging Agent Suspension A sample of an effluent containing algae was tested for clarification. The charge of the untreated effluent was $-900$ $\mu mol_c$ $L^-$. Applying coagulant NC21Z 2.5% suspension at different doses ranging from 0 to 400 µL coagulant suspension per 50 mL of algae effluents (equivalent to 0-1400 $\mu mol_c$ $L^{-1}$) it was found that efficient clarification was obtained at an added volume of 50 µL coagulant (equivalent to +890 $\mu mol_c$ $L^{-1}$). At lower or higher added amounts, less efficient effect was obtained. The results in FIG. 3 show that, 10 minutes after addition of the coagulant (amounts as µl per 50 ml effluents) the evaluated added coagulant dose yields indeed an efficient algae aggregation.

Example 3

Treatment of Olive Oil Mill Wastewater with Calculated Dosages of Various Nanocomposites/bridging Agent Suspensions The feasibility of method described in Example 1 was tested in highly charged raw OMW (initial charge of $-5400$ $\mu mol_c$ $L^{-1}$) treated with 5% suspensions of three different nanocomposites: (i) NH21 (low charge based on 800 mg chitosan per g sepiolite), (ii) NC19 (medium charge based on 500 mg poly-DADMAC per g sepiolite) and (iii) NC26 (high charge based on 2200 mg poly-DADMAC per g sepiolite) to which 10 g/L of PQ15 emulsion was added, thus forming the coagulants NH21Z, NC19Z, and NC26Z, respectively. FIG. 4 shows the light transmission of OMW after 2 min of centrifugation with the different doses of the coagulants. Table 2 summarizes the charge of NH21Z, NC19Z, or NC26Z and the calculated doses needed to neutralize the highly charged OMW.

TABLE 2

Charges and calculated doses of coagoflocculant required to neutralize highly charged OMW

|  | Charge (mmol $L^{-1}$) | Needed volume of coagoflocculant (ml $L^{-1}$) |
|---|---|---|
| raw OMW | −5.2 |  |
| Low-charge coagoflocculant (NH21Z) | 63.5 | 81.9 |
| Medium-charge coagoflocculant (NC19Z) | 124 | 41.6 |
| High-charge coagoflocculant (NC26Z) | 589 | 8.8 |

It can be seen from FIG. 4 and Table 2 that when the doses of added coagulant were close to the calculated required doses (8.8, 41.6 and 81.9 ml coagulant suspension $L^{-1}$ effluent of low-, medium- or high-charge coagulant, respectively), light transmission of the effluent as measured by the dispersion analyzer was considerably higher than at the other doses, indicating efficient colloid aggregation and clarification of the effluent. Measurements at longer times showed decreased differences between treatments. However, even after 10 min of centrifugation, the optimal treatments were those in which the charges of the effluents and coagulants were equalized.

Example 4

Treatment of OMW Effluents with a Nanocomposite, a Bridging Agent, or a Nanocomposite/bridging Agent Combination OMW was treated with: (i) nanocomposite NC26 (NC), (ii) bridging agent PQ15 (BR), or (iii) a combination of both (NC/BR), by adding: (i) 0.4 ml $L^{-1}$ of the 5% NC suspension; (ii) 2 ml $L^{-1}$ of the 2% BR) suspension; (iii) 0.4 ml $L^{-1}$ of the 5% NC suspension and 0.8, 1.2, 1.6, 2.0 or 2.8 ml $L^{-1}$ of the 2% BR suspension. The particle size of the flocks obtained after each treatment was measured with a Mastersizer laser diffraction particle sizing instrument. FIG. 7 shows the particle size distribution measured for (i) raw OMW (red -•), which had a large fraction of the particles (21%)<10 μm, and only a small part (24%)>100 μm; for the NC suspension (NC, --), for which the smaller fraction of the particles almost disappeared (only 2.1%<10 μm), but there were still 63%<100 μm, handicapping fast filtration; for the bridging agent (BR, black ••••) added alone for which very large flocks were formed, but small particles remained in large amounts (18.3%<10 μm); for the combinations NC/BR which yielded improved results, up to a ratio of 1:5 of the NC:BR. Above this ratio, results remained unchanged. At added amounts of 0.4 NC and 0.8 BR (a ratio NC/BR 1:2; gray --) still 0.8% of the particles were <10 μm and 35% of the particles were <100 μm, but increasing the amount of BR to 1.2 ml $L^{-1}$ (a ratio NC/BR 1:3, red —) resulted in that the smallest particles were about 30 μm and less than 8% of the particles were <100 μm. At NC:BR ratios of 1:5 (0.4 NC+2.0 BR, —) very good results were observed: for all cases the smallest particles observed were >70 μm, less than 1% of the particles were <100 μm and less than 5% of the particles were <200 μm, allowing very efficient and fast filtration. Larger NC/BR ratios, e.g. 1:7 (0.4 NC+2.8 BR, black --) did not improve the results.

The combination of the nanocomposites with the bridging agent increased also the velocity of the process, i.e., the formation of aggregated flocks. Olive oil mill wastewater (5 ml $L^{-1}$) was treated with various combinations of NC/BR in which the amount of the polymer per g clay varied in the NC with 2% BR suspension (NC100+BR, NC160Z+BR, NC320+BR, NC400+BR, NC600+BR and NC1000+BR) or without adding the BR suspension (NC100, NC160, NC320, NC400, NC600 and NC1000) and light transmission was measured 1 minute after addition of the coagulant at a relative acceleration force of 5 g. As shown in FIG. 8, the bridging agent (BR) alone did not clarify the OMW, but when added with the nanocomposites (NC+BR) yielded improved and very fast clarification. It should be emphasized that after 10 min the samples reached the same transmission with or without addition of the bridging agent. Thus, the main influence of the bridging agent in addition to aggregating the flocks, is in speeding the process.

Example 5

Treatment of Cowshed Effluents with a Nanocomposite, a Bridging Agent, or a Nanocomposite/bridging Agent Combination Cowshed effluents were treated with NC26 (NC), PQ15 (BR) or a combination of both (NC+BR). It can be clearly observed from FIG. 9 that BR alone did not yield clarified effluents, but formed larger and better organized flocks when combined with the nanocomposite (NC+BR). The nanocomposites without the bridging agent (NC), on the other hand, yielded very good clarification, but the flocks observed at the bottom of the tube were small and could only be filtered using a 50 μm sieve. Thus, only the combination of the nanocomposites and the bridging agent together yielded good clarification and well organized, firm and large flocks.

Example 6

Comparison of Various Treatments of Effluents on Flocks Stability 6.1 Cowshed Effluents In order to compare the efficiency of the treatment according to the present invention and of regular treatments, and also to evaluate costs, three possible options were tested on cowshed effluents:
(i) NC—Nanocomposites/bridging agent (NC21Z, based on 2.5% sepiolite suspension, 800 mg commercial poly-DADMAC per g clay, and 1% w/w commercial Zetag® 8848FS as a bridging agent);
(ii) AL—solution of 40% aluminum sulfate (+108,000 $\mu mol_c$ $L^{-1}$);
(iii) PD—solution of 10% commercial poly-DADMAC (+620,000 $\mu mol_c$ $L^{-1}$) (Magnafloc® LT 35 (40% solution) diluted 1:4.

The first experiment aimed to obtain the optimal dose for each treatment. Three different coagulants and flocculants were added at doses equivalent to 25, 550, 100, 125 and 200% of those required to neutralize the colloids in 10 ml effluents. Measurements were performed with a LUMiSizer dispersion analyzer, at 200 RPM (equivalent to 5 g centrifugal acceleration). In order to measure the efficiency of the clarification, light transmission through the upper 70% of the test tube was measured after 30 and 150 s (equivalent to 2.5 and 7.5 min at normal gravity). Raw cowshed effluents (CW) were treated with NC21Z coagulant (NC), aluminum sulfate (AL) or commercial polyDADMAC (PD). It can be seen from FIG. 10 that only the nanocomposites/bridging agent treatment achieved clarification with low standard deviation at very short times (30 s, FIG. 10, white bars). The two additional treatments (AL or PD) yielded relatively good clarification (better for the alum, and mediocre results for the commercial PD) but only at longer sedimentation times (150 s, FIG. 10, black bars).

According to the results, the following optimal treatments were chosen for the next experiment: nanocomposites/bridging agent (NC) at 16 mL/L, alum (AL) at 2.0 ml/L and commercial PD (PD) at 0.6 mL/L Table 3 shows the evaluated cost of the three chosen treatments. All cost evaluations were performed based on the retail cost in Israel of the raw materials for each treatment. It can be seen that all costs are of the same order of magnitude: the alum treatment is the cheapest whereas the proposed nanocomposites/bridging agent (NC) treatment is cheaper than commercial PD application at the efficient doses.

In another experiment, the chosen doses were added to the cowshed effluents in 50 ml test tubes. After mixing the coagulant with the effluents, and waiting for ten minutes to allow spontaneous sedimentation, turbidity of the cleared effluents was measured. FIGS. 11A-11B show comparative results for the clarification of cowshed effluents, before (11A) and after (11B) filtration through a 212 μm screen. As shown in Table 3, and FIG. 11A the supernatant of all three treatments achieved before filtration a >95% turbidity removal. Afterwards the treated samples were filtered through a 70 mesh (212 μm) screen. The more notable advantage of the nanocomposites/bridging agent use was observed at this stage (Table 3 and FIGS. 11A-11B): whereas the nanocomposites/bridging polymer (NC) treatments yielded filtrated effluents with only 10 NTU of turbidity, the two other treatments formed only small and unstable flocks that were not stopped by the 212 μm screen, thus filtrated effluents contained very large amounts of suspended material. Only the use of a 50 μm filter could reduce turbidity in AL and PD treatments to approximately 100 NTU, however as mentioned above, such fine screen requires the use of pressure in order to make the effluents to pass through the screen.

The experiment described above demonstrates that only the use of nanocomposites/bridging agent yields the formation of large and stable enough flocks that allows separation by simple filtration with a large pores screen. Considering that the cost of the treatment is similar, the advantage of nanocomposites/bridging agent is obvious.

Similar results were obtained with various effluents as summarized in Table 4. In all cases a suitable amount of coagulant was added and after 2-10 min effluents were filtered through a 200 micron screen.

TABLE 4

Summary of effluents tested with combinations of nanocomposites and bridging polymers

| | Number of samples tested | Before treatment | | Percent removed | |
|---|---|---|---|---|---|
| Effluent | | TSS (mg/l) | COD (mg/l) | TSS (%) | COD (%) |
| Winery | >200 | 1000-2500 | 3000-20000 | 93-99 | 10-30 |
| Olive mill | >200 | 6000-50000 | 15000-70000 | 90-98 | 25-60 |
| Algae | 10 | 500-5000 | ND | 97-99 | ND |
| Dairy | 5 | 1000-4000 | 1000-12000 | 95-99 | 20-60 |
| Cowshed | 12 | 2000-20000 | 3000-15000 | 96-99 | 65-95 |

ND = not detected 6.2 Olive Oil Mill Wastewater

A cost evaluation on cowshed effluents is presented in Table 3 above. OMW is a considerably more difficult to treat effluent. OMW was treated with 2.5% NC26 suspension, NC26Z (NC26 nanocomposite with 10 g/L of PQ15 (commercial inverse emulsion), an alum solution, and commercial PD (FL45) (data not shown). In all cases the dose chosen was the dose that yielded the best effect after 15 minutes (whereas for NC26Z the effect was obtained almost immediately). It can be seen from Table 5 that even at retail prices the use of this method is cost effective when compared with other, considerably less effective, treatments.

TABLE 5

Cost evaluation for the treatment of OMW

| | price €/m³ |
|---|---|
| NC26 5%, 5 ml/L | 4.28 |
| NC26Z 5%, 5 ml/L | 4.83 |
| Alum 40%, 46 ml/L | 23.00 |
| FL45- PD 40%, 2 ml/L | 5.76 |

TABLE 3

Comparative results for the clarification of cowshed effluents, before and after filtration through a 212 μm screen

| | | before filtration | after 212 μm filtration | | | |
|---|---|---|---|---|---|---|
| | price €/m³ | turbidity (NTU) | turbidity (NTU) | TSS (mg/L) | VSS (mg/L) | COD (mg/L) |
| raw not filtered | | 2200 | | 4480 | | 5463 |
| raw filtered | | | 1510 | 2900 | 1620 | 1520 |
| NC21Z 2.5%, 16 ml/L | 1.36 | 11 | 10 | 73 | 33 | 60 |
| Alum 40%, 2 ml/L | 1.00 | 19 | 1480 | 3630 | 1840 | 1790 |
| PD 10%, 2.4 ml/L | 1.73 | 44 | 807 | 3230 | 1880 | 1160 |

Example 7

Fast Sedimentation Obtained by Using a Combination of Nanocomposites in Excess and an Oppositively Charged Bridging Agent OMW effluents after bioreactor COD reduction with TSS=3220 mg/L, turbidity >600 NTU and an initial charge (measured with a PCD)=−1130 mmol$_c$/L were treated by adding nanocomposites in slight excess followed by addition of a bridging agent with an opposite charge from the nanocomposite. Based on the charge of the nanocomposites according to the method of the invention, efficient charge neutralization should be obtained using, for example, 54 μL of a 5% suspension of nanocomposite NC19 with a charge of +215000 mmole$_c$/L per 10 mL of OMW effluents.

The experiment was performed as follows: to raw OMW effluent (10 mL) a 5% NC19 suspension (60 μL) was added. The test tube was stirred in a vortex for 10 s, followed by addition of a 10% analytical PAM (p) solution (0-30 μL), which at neutral and basic pHs (>5.5) is slightly negatively charged. It can be clearly observed from FIG. 12 that untreated raw effluents ("blank") remained turbid; addition of 60 μL of NC19 nanocomposites suspension ("N60") alone yielded an efficient clarification after 10 min of centrifugation (equivalent to 50 min at normal gravity); and addition of 5 or 15 μL of the anionic bridging agent PAM (e.g. "N60+p5" or "N60+p15") accelerated the sedimentation more than 5 folds. For example, adding 15 μL of PAM yielded already a transmission of almost 55% after only 2 min, and even after 1 min only values of >40% transmission were observed (although with very large standard deviation), whereas treatment with the nanocomposites ("N60") without the bridging agent PAM yielded transmissions of only 26% and 12% after 2 and 1 min, respectively.

FIGS. 13A-13F show recorded evolution (from left to right) of time dependent transmission profiles of the experiment. Profiles were taken every 5 s at RCF of 5 g (200 rpm), for 15 minutes. A particle migration due to centrifugal force resulted in a variation of the local particle concentration and correspondingly local and temporal variations of light intensity through the sample occur. Each 5 s a light intensity profile of each individual sample was recorded by a sensor. Sensor resolution allowed detecting small changes of the position of an interface between two phases. The first profile (bottom line in each Figure) depicts the position of the interface immediately after the start of the centrifuge (5 s). The overlay of profiles at the right side (thickening of the line) documents that the sedimentation process came to its end and marks the position of the sediment (Lerche, 2002). The fluctuation in position of approximately 108 mm indicates the meniscus between the suspension and the air above, whereas decreased light intensity in positions >125 mm indicates the sedimented particles. Sediment thickness can be evaluated according to the light intensity values at the bottom of the tubes.

Figure 13A:
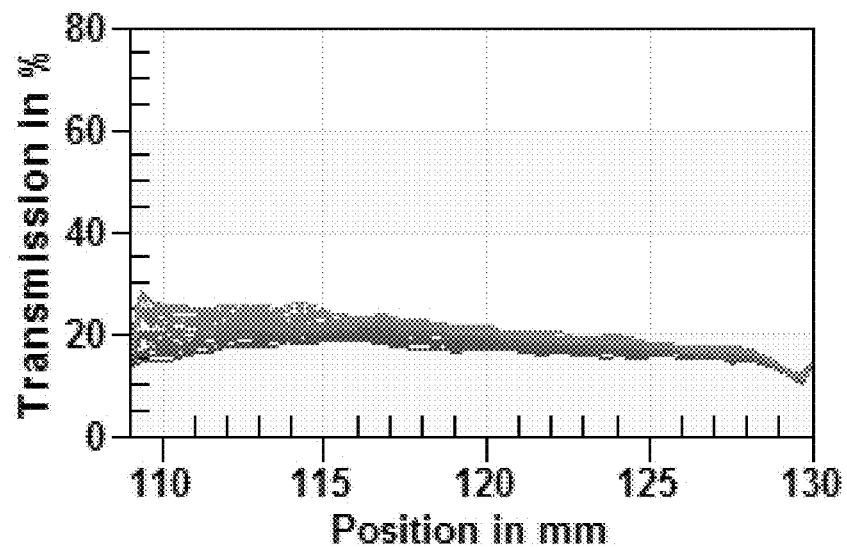
Figure 13B:
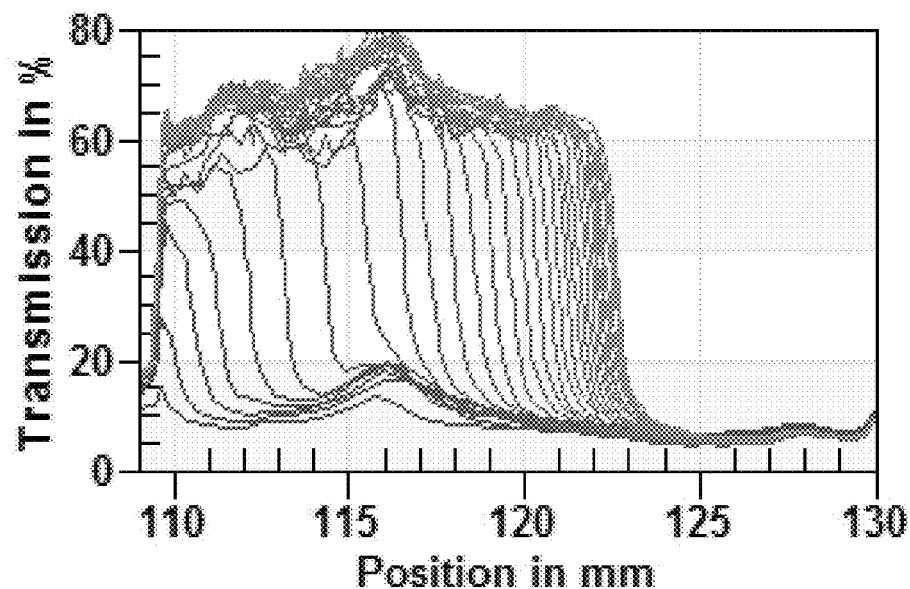
Figure 13C:
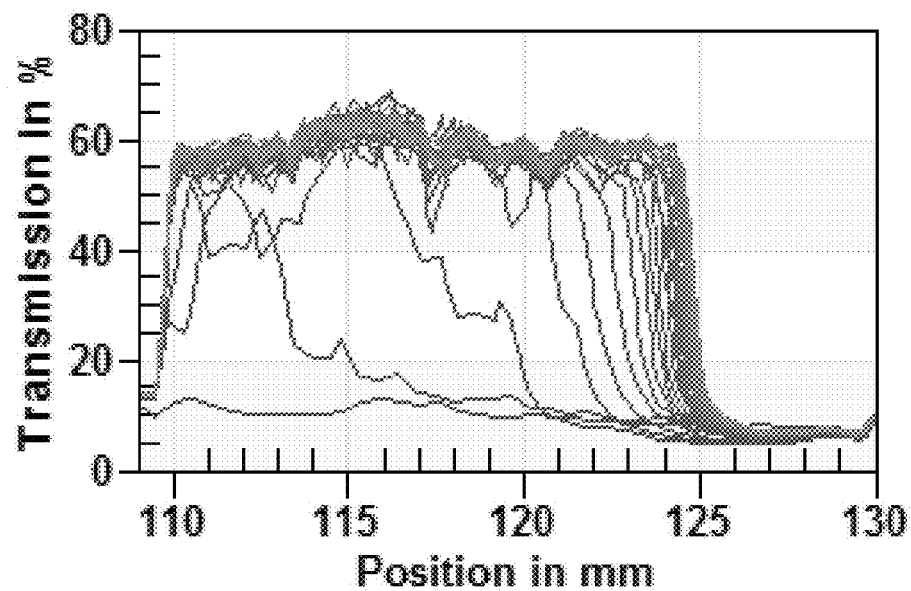
Figure 13D:
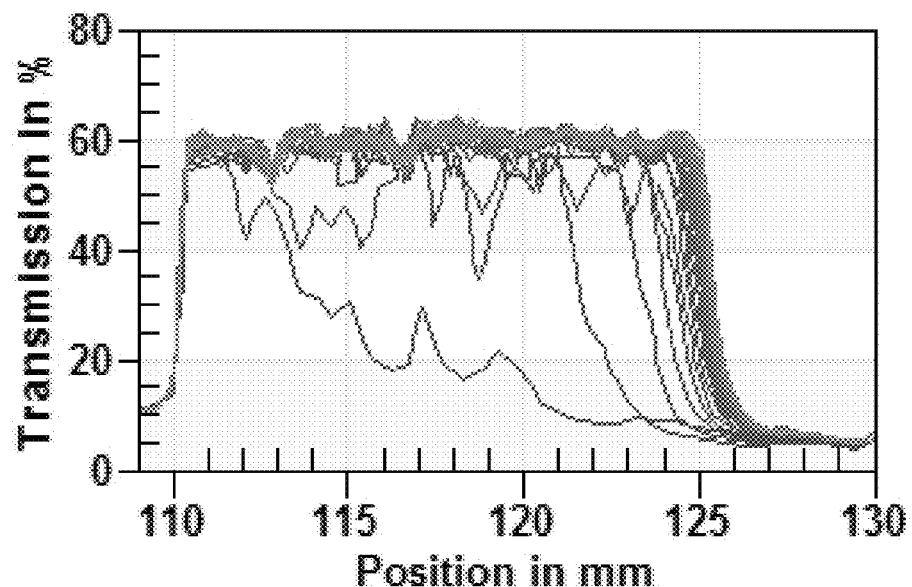
Figure 13E:
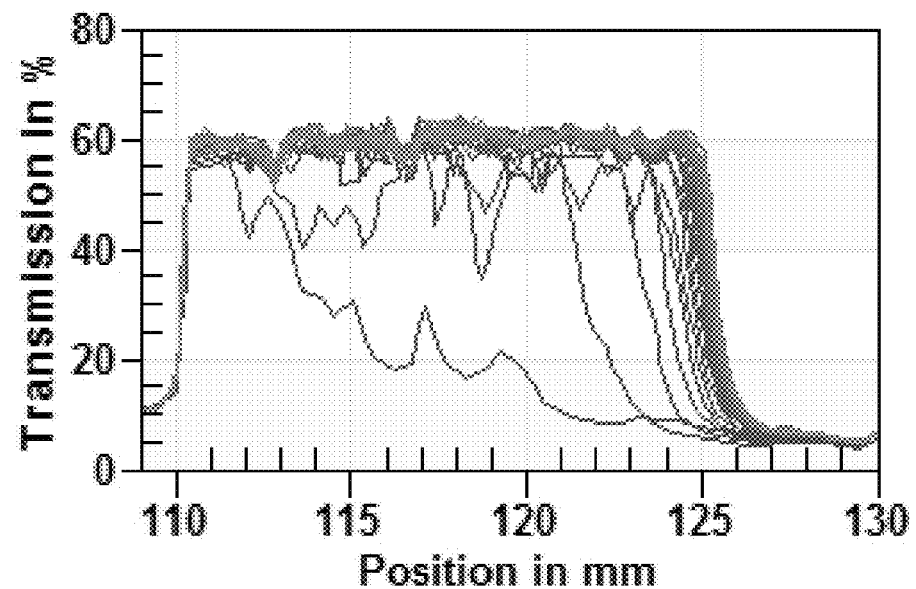
Figure 13F:
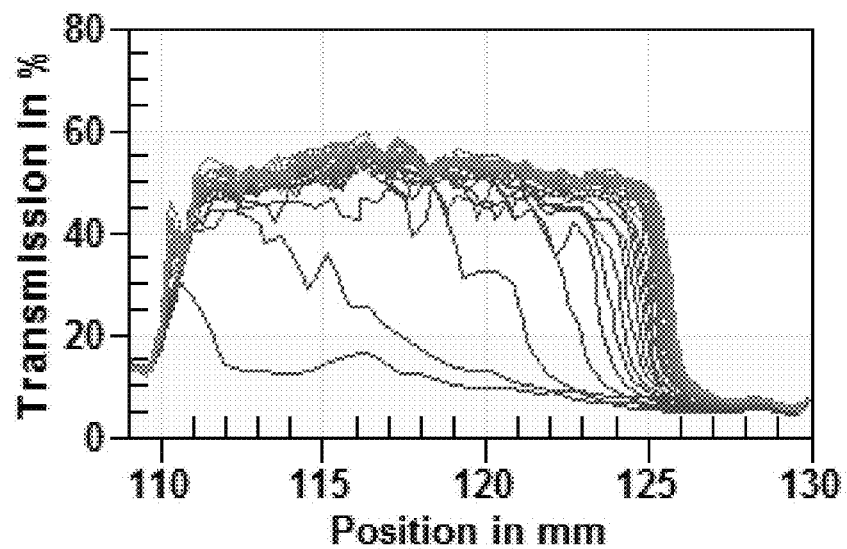

It can be seen from FIGS. 13A-13F that intensity through the untreated OMW sample (FIG. 13A) almost did not change due to centrifugation. Addition of NC19 nanocomposites at the slightly overneutralizing amount of 60 μL per 10 ml (without addition of the bridging polymer) yielded a slow but constant sedimentation (FIG. 13B). Addition of PAM at any amount made the sedimentation considerably faster (FIGS. 13C-13F), whereas the optimal effect was observed at 15 μL (FIG. 13E). At increased PAM amounts (30 μL of PAM) a slight decrease in the performance was observed, emphasized by the final light transmission (see the horizontal line in FIG. 13F and FIG. 13A) that decreased from 57% to 50%. Such an effect is ascribed to a possible repulsion between particles due to the negative overcharge of the bridging agent PAM.

Example 8

Clarification of OMW Effluents and Flocks Stability Using Nanocomposites and Either a Positively or Negatively Charged Bridging Agent The present example shows an additional aspect of the improved performance obtained according to the present invention. OMW effluents having a charge of −1130 mmole$_c$/L were tested for the stability of flocks and possible filtration after treatment with a 5% nanocomposite suspension based on NH21 with a charge of 157000 mmole$_c$/L. For neutralization of 10 ml of OMW effluents, 74 μL of NH21 are needed. Raw OMW effluent (blank) and three treated OMW samples (10 ml) were compared: neutralization with 75 μL NH21 (NH), NH/PQ (60 μL NH21 suspension (underdose) and 100 μL of 1% positively charged PQ15), and NH/PAM (90 μL (overdose) of NH21 suspension with subsequent addition of the negatively charged PAM (15 μL of a 10% PAM suspension)).

It can be seen from FIGS. 14A-14B that in all treatments (except the blank) flocks formation was observed, but for OMW effluents treated solely with the NH21 nanocomposites (NH) only a small part of the volume was clarified. OMW effluents treated with the NH21 nanocomposites and either the positively PQ15 or the negatively charged PAM bridging agent (NH/PQ or NH/PAM) yielded good clarification. FIG. 14B shows the same samples 60 min after preparation/addition of NH, NH/PQ or NH/PAM. It can be observed that all three treatments exhibit relatively nice clarification. Thus, one advantage of addition of the bridging agent concept is the velocity of clarification.

Another advantage of using nanocomposites with a bridging agent can be observed after filtering the treated samples (10 min after) through a 70 mesh (212 μm) screen. As can be seen from FIG. 15 and Table 6 the treatments with NH21 nanocomposites and either the positively charged PQ15 or the negatively charged PAM bridging agent (NH/PQ or NH/PAM, respectively) yielded filtrated effluents with TSS of less than 100 mg/L, while the blank and NC21 nanocomposites alone (NH) treatment formed only small and unstable flocks that were not stopped by the 212 μm screen and thus the filtered effluents contained very large amounts of suspended material (TSS>1300 mg/L). Only the use of a 50 μm filter could reduce turbidity in NH treated samples, whereas blank sample was not influenced by filtration at all. As mentioned above, screens 50 μm or finer require the use of pressure in order to make the effluents pass through the screen.

TABLE 6

Comparative results for the clarification of OMW effluents, before and after filtration through a 212 μm screen

|  | clarified effluents TSS (mg/L) before filtration | total TSS (mg/L) after 212 μm filtration |
| --- | --- | --- |
| blank | 2720 | 2100 |
| NH21 5% 75 μL | 50 | 1330 |
| NH21 5% 60 μL + PQ15 | 55 | 75 |
| NH21 5% 90 μL + PAM | 60 | 85 |

Example 9

Clarification of Piggery Effluents Using Nanocomposites or a Combination of a Nanocomposite and a Bridging Agent The efficiency of nanocomposites for the TSS removal was tested on piggery effluents (from Lahav Piggery, Israel) from two different sources: (a) effluents sampled from the sedimentation pond, and (b) effluents sampled from the fattening area. As a preliminary measurement in order to evaluate the amount and type of a nanocomposite needed to perform an efficient treatment, charge measurements were performed as described in Method (a) above. The doses needed for neutralization of piggery effluents with a NC24 2.5% nanocomposite suspension based on 2.5% S9 sepiolite and 1800 mg PD per gram clay are summarized in Table 7. A commercial formulation consisting of an inversed emulsion of PQ15 at 0.25% concentration was used as a bridging polymer (BP).

TABLE 7

Calculated needed doses of NC24 nanocomposite for the clarification of piggery effluents

| Piggery effluents source | Average charge ($\mu mol_c\ L^{-1}$) | Std dev (%) | Neutralization dose of NC24 2.5% ($mL\ L^{-1}$) |
|---|---|---|---|
| Sediment pond | 4987 | 2.65% | 14.5 |
| Fattening area | 2527 | 3.56% | 7.3 |

Table 8 shows results for treatment of piggery effluents from two sampling sites with NC24 nanocomposite (Examples 9.3-9.4, and 9.13), with bridging agent PQ15 alone (Examples 9.2 and 9.7), or with various combinations of NC24 and PQ15 (Examples 9.5, 9.8-9.12). In Examples 9.3 and 9.13 the exact dose of the NC24 nanocomposite was added for the neutralization of the effluents, and the samples were allowed to sediment for about 30 min. Measurements were performed from the supernatant (S*). In Examples 9.7-9.12 the influence of the dose of NC24 nanocomposite was tested at the same BP dose. The samples were screened through a 200 µm filter, except for the samples of Examples 9.3, 9.11 and 9.13 which were allowed to sediment for 30 min and TSS and COD were measured in the supernatant.

In conclusion:
(i) TSS removal is slightly worst (80-90%) than with other effluents (>95%, Table 4 above). However, when no filtration was applied, TSS values were considerably lower (~100 ppm), indicating that sedimentation of the flocks might be the most effective procedure for clarification of those effluents.
(ii) COD removal is similar to the observed in cowshed (40-70%). Samples from sediment site yielded better COD removal.
(iii) Bridging agent alone did not yield significant reduction in TSS and COD.
(iv) Addition of the suitable amount of NC24 nanocomposite alone followed by filtration through a 50 µm filter (Example 9.4) did not deliver the same efficiency as the sedimentation (Example 9.3), indicating existence of either smaller or less stable flocks.
(v) In cases where the bridging agent was used, high nanocomposite doses (80%) were worse than a suitable range (20-60% of the needed for full neutralization). With no bridging polymer—100% neutralization with sedimentation or fine filtering delivered very good results.

Example 10

Use of Nanocomposites for the Removal of Suspended Material in Saline Effluents, Feed Water and Brine from Desalination Facilities Use of desalination processes is expected to increase constantly. Colloidal material in the feed of desalination facilities is caused mainly by clay minerals covered by organic materials and surfactants, thus pretreatment influences cost efficiency of desalination. The brine contains also remaining coagulants, antiscalants, and all the colloidal material removed from the feed water and accumulated in the filters.

Saline wastewater from industries as pickles or canned vegetables, fish and meat, is usually characterized by low pH (3.5-6), high salt content (mainly NaCl 2500-14000 mg/L) and high concentrations of dissolved and suspended solids, composed mostly of organic matter.

In the present example the ability of nanocomposites to reduce suspended solids in high salt concentration water was

TABLE 8

Results for treatment of piggery effluents from two sampling sites

| | Site | NC24 dose (ml/L) | BP dose (ml/L) | Filter (µm) | TSS ppm | TSS percent removed | COD ppm | COD percent removed |
|---|---|---|---|---|---|---|---|---|
| Example 9.1 | sediment | raw | | | 1890 | | 5103 | |
| Example 9.2 | | 0 | 50 | 200 | 1540 | 18.5% | 4333 | 15.1% |
| Example 9.3 | | 4 | | S* | 117 | 93.8% | 1810 | 64.5% |
| Example 9.4 | | 4 | | 50 | 478 | 74.7% | 1889 | 63.0% |
| Example 9.5 | | 0 | 50 | 200 | 400 | 78.8% | 1709 | 66.5% |
| Example 9.6 | fattening | none | | | 1261 | | 5128 | |
| Example 9.7 | | 0 | 40 | 200 | 950 | 24.7% | 4329 | 15.6% |
| Example 9.8 | | 1.5 | 40 | 200 | 257 | 79.6% | 3488 | 32.0% |
| Example 9.9 | | 3 | 40 | 200 | 243 | 80.7% | 2907 | 43.3% |
| Example 9.10 | | 4.4 | 40 | 200 | 287 | 77.2% | 2885 | 43.7% |
| Example 9.11 | | 5 | 40 | S* | 107 | 91.5% | 3316 | 35.3% |
| Example 9.12 | | 6 | 40 | 200 | 450 | 64.3% | 2714 | 47.1% |
| Example 9.13 | | 7 | | S* | 95 | 92.5% | nd | |

S* = supernatant tested, in order to check the feasibility of the use of such coagulants for the pretreatment of saline industrial effluents, desalination pretreatment, and desalination brine suspended material removal before rejecting the brine back to the sea.

Polluted saline effluents were synthetically prepared by mixing Mediterranean Sea water with 10% (by weight) cowshed effluents. The final effluents were measured for turbidity (>800 NTU) and TSS (600 mg/L).

The procedure described in the method of the invention for determining the type and dosage of coagulant cannot be applied in such high salt concentration liquids due to the very low absolute value of electrokinetic potential caused by the very high ionic strength. Thus, direct clarification "trial and error" experiments were performed using the LUMisizer dispersion analyzer.

The experiments were performed using (i) nanocomposite suspensions based on 5% sepiolite clay and amounts of polyDADMAC ranging between 0.02-0.5 g polymer per g clay (denoted as NC6 up to NC19); or (ii) nanocomposites based on 5% sepiolite clay and amounts of the cationic biopolymer chitosan ranging between 0.02-0.4 g polymer per g clay (denoted as NH6 up to NH18). In both cases, a constant dose of 10 mL coagulant suspension per L effluents was used.

FIG. 16 shows light transmission of the effluents treated with various NC nanocomposites. As can be seen from FIG. 16, the NC nanocomposites were not effective in clarifying the effluents, and the light transmission measured remained similar to the initial value for all the samples. SW denotes the synthetically prepared polluted effluents.

FIG. 17 shows light transmission of the effluents treated with various NH nanocomposites. As can be seen from FIG. 17 the NH nanocomposites with low amounts of polymer (less than 0.07 g/g) were not effective in clarifying the effluents, but treatment with NH nanocomposites with higher biopolymer/clay ratios increased the light transmission considerably, indicating an efficient clarification.

In order to perform an optimization of the dose, NH18 (5% sepiolite with 0.4 g chitosan per g clay) was applied at doses ranging from 5 to 35 ml suspension per L effluent. FIG. 18 shows light transmission measured after several periods of time of the effluents treated with various doses of NH18 nanocomposites. It can be seen from FIG. 18 that SW (polluted saline effluents) is stable, and the measurements after 2, 5, 10 and 20 min did not influence the light transmission. Low doses (5 ml/L) of NH18 did not achieve a considerable improvement, but for doses of 10 mL/L and higher, a significant clarification was observed (FIG. 18). It is interesting to notice that at a dose of 10 mL/L a very fast clarification was observed. Higher doses (20-30 mL/L) of NH18 yielded a slower process, but in the end clearer effluents were achieved. At the highest dose (35 mL/L) of NH18 a slight decrease in the performance was observed.

The results demonstrate the ability of nanocomposites to clarify saline effluents even at a level of 30-35 g/L dissolved salts. It is interesting to note that nanocomposites that were very effective in "fresh" water (sepiolite+poly-DADMAC) did not deliver any clarification in saline effluents. We assume that the inefficiency of the NC particles is caused by the high $Cl^-$ concentration influencing differently the charge of the quarternary ammonium groups that are in a different configuration in both polymers (polyDADMAC and chitosan).

Example 11

Treatment of Bromine Industries Effluents

The efficiency of the method of the present invention in pretreatment of saline bromine industries effluents was tested. Twenty five samples of bromine industries effluents, from 5 consecutive days (24-28/6/2014) at 5 sampling hours each (8:00, 12:00, 16:00, 18:00, and 22:00) were received (source in Israel) and treated. All samples contained very high salts content (0.5-2% Na, 0.5-1.5% Cl and 0.3-1.0% Br, etc.).

Most sample bottles received contained clear effluents with a sediment at the bottom. A few samples contained partly turbid effluents with sediment at the bottom. Part of them contained very large and strong flocks that did not break when agitating the bottles. Initial turbidity of all effluents after agitation was very high (>1500 NTU), and turbidity remained stable for at least 3 h. Due to the high salinity the zeta potential of the effluent is close to zero, thus reducing considerably the sensitivity of the charge-measurement technique to determine doses. Thus, efficient treatments were evaluated by performing a preliminary measurement with the LUMisizer instrument.

The treatments were performed as follows: (1) A low dose of (2 ml/L) NC26 5% (50 g/L sepiolite combined with 2.2 g polyDADMAC per g clay) was added to an effluent to surely obtain positively charged colloids, followed immediately by a dose of 20 ml/L of a commercial poly-acrylamide co acrylic acid anionic compound (ZETAG® 4145 by BASF®) 0.2% solution added as a "bridging polymer/agent" (BP). Flocks were formed immediately (5-10 s), occupying 10-30% of the volume. Initially, due to the agitation technique and introduction of air into the flocks most of the flocks floated. However, after a few hours they sank. Separation was performed with a 200 microns screen. (2) A dose of 20 ml/L NH24P 2.5% (25 g/L sepiolite combined with 1.8 g chitosan per g clay) was added to effluents and formed large and nice flocks without the need of addition of a bridging polymer. Flocks were formed slightly slower than in (1) above but still were formed very fast (15-30 s), occupying 20-50% of the volume. As above, initially most of the flocks floated, but after a few hours they sank. Separation was performed with a 100 microns screen. The smaller holes screen was chosen due to the fact that no bridging polymer was used and small flocks were formed. (3) Both tests above were compared with one dose of 2.8 ml/L of alum 50% solution ("the regular treatment"), followed by the same dose of BP solution mentioned above (20 ml/L). Flocks were formed similar to above (15-30 s), occupying 20-50% of the volume. All flocks were sedimented in a few minutes. Samples were also filtered with a 200 microns screen, for comparison with treatments (1) and (2).

In Table 9 below the parameters are reported in "classes" of:

Turbidity: "None": >5 NTU; "very low": 5-10 NTU; "low": 10-20 NTU; "medium-low": 20-30 NTU; "medium": 30-50 NTU; "medium-high": 50-75 NTU; "high": 75-150 NTU; and "very high": >150 NTU.

Sludge Volume Index (SVI) after Filtering: "None": no noticeable sludge; "low": <5% of the total volume; "medium": 5-10% of the total volume.

Results and Conclusions:

ALUM+BP: (a) The regular treatment of alum+BP formed flocks fast with high density that sank, occupying 30-50% of the volume, and leaving in all tested cases a clear supernatant, but a thick sludge. (b) Filtering of the treated effluents was in about 75% of the samples partially ineffective since the formed flocks were broken partially when passing the filter, and in some cases 10% of the filtered volume was occupied by flocks. In about 20% of the samples the turbidity increased considerably due to the disintegration of a part of the flocks while filtering. After waiting for 1-2 h, the floccs sank, and the sample was clarified, but the SVI was relatively high, imposing for high TSS.

Chitosan Based Nanocomposites (NH24P) without Addition of BP: (a) in this treatment the flocks were formed fast without adding BP. Flocks floated at the beginning and after a few hours they sank. This effect can be controlled by a slower mixing (introducing less air to the flocks). (b) Filtering of the treated effluents in almost all the samples was partially ineffective: the formed flocks broke partially passing the filter, whereas in most cases less than 5% of the filtered volume was occupied by flocks. In some (1 or 2) of the samples the turbidity was increased, but only to values below 50 NTU.

Regular (polyDADMAC) Based Nanocomposites (NC26) Followed by an Addition of a Bridging Polymer (BP): (a) In this treatment the flocks were formed very fast. Floccs floated at the beginning and after a few hours sank. The floating effect can be controlled by a slower mixing (introducing less air to the flocks). (b) Filtering of the effluents in almost all the samples was very effective: almost no flocks passed. Only in three cases traces of flocks passed through the filter. In some of the samples (1 or 2) turbidity increased, but only to values below 50 NTU.

In summary, a treatment with a combination of nanocomposites and a bridging agent (NC+BP) ensured efficient reduction in turbidity and sludge content in a wide range of saline effluents from bromine industry. Other treatments as (alum+BP) or chitosan based nanocomposites without a bridging polymer exhibited a very efficient treatment in some cases, but failed in others.

TABLE 9

Bromine effluents treated with NH24P, NC26 + BP, and Alum + BP

| Sample | | Turbidity (class) | | | SVI-sludge volume percentage (class) | | |
|---|---|---|---|---|---|---|---|
| | | NH24P | NC26 + BP | Alum + BP | NH24P | NC26 + BP | Alum + BP |
| day | hour | filtered | filtered | filtered | filtered | filtered | filtered |
| 24 | 08:00 | low | no | very high | medium | no | low |
| | 12:00 | very low | no | medium | medium | no | no |
| | 16:00 | no | medium | high | no | low | no |
| | 18:00 | no | medium-low | low | low | low | low |
| | 22:00 | no | medium-low | medium-low | low | no | low |
| 25 | 08:00 | no | no | medium-low | low | no | medium |
| | 12:00 | no | very low | low | low | no | low |
| | 16:00 | no | no | low | low | no | low |
| | 18:00 | very low | very low | low | medium | no | medium |
| | 22:00 | no | very low | very low | medium | no | low |
| 26 | 08:00 | no | no | very high | low | no | medium |
| | 12:00 | very low | no | medium | medium | no | medium |
| | 16:00 | no | no | medium-low | medium | no | low |
| | 18:00 | very low | no | medium-low | medium | no | no |
| | 22:00 | very low | no | low | medium | no | no |
| 27 | 08:00 | no | no | low | no | low | low |
| | 12:00 | no | no | medium-low | low | no | low |
| | 16:00 | low | no | medium-low | medium | no | no |
| | 18:00 | very low | no | medium-high | medium | no | no |
| | 22:00 | very low | no | medium-high | no | low | low |
| 28 | 08:00 | no | no | medium | medium | no | low |
| | 12:00 | medium | no | medium | medium | no | low |
| | 16:00 | medium-low | no | medium-low | medium | no | low |
| | 18:00 | very low | no | medium-low | medium | no | no |
| | 22:00 | no | no | medium-low | medium | low | low |

Example 12

Application of a Combination of a Nanocomposite and a Bridging Agent in a Continuous System This example shows that the method for pretreatment of wastewater according to the present invention can be performed in a continuous system. FIG. 19 presents a continuous system for pretreatment of wastewater with a nanocomposite and a bridging agent. The system which was designed from an effluents vessel (6), a peristaltic pump (7) that pumps effluents through a pipe at rates of 90-200 ml min$^{-1}$ To the pipe a "T" connector was added, and a second peristaltic pump (9) injects a nanocomposite suspension (8) at a dose of 1-8 ml min$^{-1}$. After about a meter of the pipe that is connected to (9) (so as to allow enough mixing of the nanocomposite) another "T" connector was added, and a third peristaltic pump (11) injects a bridging polymer suspension at doses of about 1-10 ml min$^{-1}$. Another segment of a pipe about 0.5 m was added afterwards to allow enough mixing and flocks formation, and the effluents were introduced to a "sedimenter" (12), while the clear supernatant flows to (13) (FIG. 19).

The idea of the "sedimenter" (12) is to allow the denser flocks to remain at the bottom of a vessel, while the clear supernatant flows to another vessel. The whole process is continuous and was tested with piggery, cowshed and winery effluents. Doses were determined with the evaluation techniques described in Example 6 above (Rytwo et al., 2014), while the control of the doses was performed by the injection rate of pumps (9) and (11) in relation to flow rate of pump (6).

For piggery effluents, the main effluents pump (6) worked at 135 ml min$^{-1}$. The nanocomposite used was a relatively dilute suspension of NC24 (containing 0.5% sepiolite and 1.8 g poly-DADMAC per g clay) and was injected at a rate of 4 ml min$^{-1}$. The bridging polymer used consisted of a commercial inversed emulsion of PQ15 at 0.25% concentration, and was injected at 8 ml min$^{-1}$.

For cowshed effluents the experiment was performed similarly with slightly different characteristics: the main effluents pump (6) worked at 90 ml min$^{-1}$. The nanocomposite used was the same as in the piggery effluents experiment, and was injected at a rate of 3 ml min$^{-1}$. The bridging polymer used consisted of a commercial solid polyacrylamide-quarternary ammonium co-polymer at 0.05% concentration, and was injected at 5 ml min$^{-1}$.

The concentrated winery effluents had very high TSS and COD but relatively low charge. Thus, the experiment was performed as follows: the main effluents pump (6) worked at 90 ml min$^{-1}$. The nanocomposite used was a dilute suspension of NC17 (containing 0.5% sepiolite clay and 0.32 g poly-DADMAC per g clay) and was injected at a rate of 4.5 ml min$^{-1}$. The bridging agent used was the same as in the cowshed effluents, i.e. a commercial solid polyacrylamide-quarternary ammonium co-polymer at 0.05% concentration, and was injected at 5 ml min$^{-1}$.

Table 10 below summarizes the results obtained for all samples mentioned above before ("raw") and after treatment with a combination of a nanocomposite and a bridging agent in a continuous system ("supernatant"). As can be seen, very good (more than 95%) TSS removal was observed for all cases. COD removal for piggery and cowshed effluents were also impressive in this case, even though we should emphasize that the main advantage of our invention is TSS removal and COD reduction is only a by-side effect, depending strongly on the ratio between particulates and dissolved organic pollutants in the effluents.

TABLE 10

Results for treatment of piggery, cowshed and winery effluents with a combination of a nanocomposite and a bridging polymer in a continuous system

| | | TSS | | COD | |
|---|---|---|---|---|---|
| Effluent | Sample | ppm | percent removed | ppm | percent removed |
| 1 Piggery | raw | 2833 | | 4760 | |
| 2 | supernatant | 165 | 94.2% | 1210 | 74.6% |
| 3 Cowshed | raw | 4070 | | 6890 | |
| 4 | supernatant | 65 | 98.4% | 900 | 86.9% |
| 5 Winery | raw | 15550 | | 12000 | |
| 6 | supernatant | 485 | 96.9% | 8030 | 28.0% |

Example 13

New Nanocomposites Consisting of Anchoring Particles and High/medium or Low Charge Density Cationic Polyelectrolyte In order to emphasize the possibility of preparing additional nanocomposites, comparing them with a bridging agent, and even using two nanocomposites together (one as coagulant and the other as "bridging agent"), a series of 'polymer'-sepiolite sepiolite combinations was prepared. All new nanocomposites were tested for the clarification of raw cowshed effluents (Kfar Blum Cowshed (IL) collected during July 2014). In all examples the bridging polymer/agent (BP) used was a 0.5 g L$^{-1}$ suspension of a commercial solid copolymer of acrylamide and quaternized cationic monomer (Zetag® 8185, BASF®, Germany). The following parameters were measured on the clarified effluents: (a) turbidity 30 m and 3 h after application; (b) COD; (c) total N; and (d) chlorine concentration.

Charge of the effluents and of the nanocomposites suspensions was also measured in order to evaluate the amounts of coagoflocculant needed to achieve an efficient clarification according to the procedure described in Example 1.

13.1 Raw Effluents and the Use of a Bridging Polymer/agent (BP) Only

In order to test the efficacy of a bridging agent alone on the clarification of raw cowshed effluents, the same doses of 20 ml BP suspension were added. As can be seen from Table 11 below, the addition of BP did not influence the COD or total N values. Due to the relatively low charge of the bridging agent, volumes needed for neutralization are very large, making such neutralization not possible. Thus, even though a considerable reduction in turbidity was observed, values are still very high. A contribution of Cl and P by the bridging polymer was observed. Such contribution is indeed very interesting, since the Cl coming from BP seem to be bound to the flocks made by the added nanocomposites (see the results below).

TABLE 11

Cowshed effluents treated with 20 ml BP only.

| Parameter | Units | Raw | BP 0.05% |
|---|---|---|---|
| Charge | mole$_c$ L$^{-1}$ | −2.9 | 9.8 |
| Concentration needed for neutralization | ml L$^{-1}$ | — | 296 |
| Cl | mg L$^{-1}$ | 2740 | 3330 |
| Added nanocomposite | ml L$^{-1}$ | — | — |
| Added BP | ml L$^{-1}$ | — | 20 |
| COD | mg L$^{-1}$ | 5809 ± 205 | 5755 ± 503 |
| Total N | mg L$^{-1}$ | 164 ± 5 | 160 ± 7 |
| Turbidity | NTU | 3100 ± 71 | 1695 ± 21 |

13.2 Pretreatment of Raw Cowshed Effluents with Poly-DADMAC (NC) or Chitosan (NH) Based Nanocomposites In previous examples we presented the use of nanocomposites based on poly-DADMAC or chitosan bound to sepiolite clay. In order to compare with the new proposed nanocomposites, we prepared suspension based on those combinations. The nanocomposites were applied to the cowshed effluents with or without the bridging agent. The measured parameters are presented in Table 12 below.

TABLE 12

Cowshed effluents treated with NC24 or NH19

| Parameter | Units | Raw | NC24 1.8 g/g | | NH19 2.5% 0.5 g/g | |
|---|---|---|---|---|---|---|
| Polymer | | | PD | | Chitosan | |
| Charge | $mole_c\ L^{-1}$ | −2.9 | 136 | | 53 | |
| Concentration needed for neutralization | $ml\ L^{-1}$ | | 21.3 | | 54.7 | |
| | | | without BP | with BP | without BP | with BP |
| Added nanocomposite | ml/L | | 21 | 17 | 55 | 50 |
| Added BP | ml/L | | | 20 | | 20 |
| Cl | $mg\ L^{-1}$ | 2740 | 3280.0 | 1990.0 | 1960.0 | 2650 |
| COD | $mg\ L^{-1}$ | 5809 ± 205 | 2526 ± 382 | 2045 ± 114 | 5694 ± 313 | 4969 ± 375 |
| | % removed | | 56.5% | 64.8% | 2.0% | 14.5% |
| Total N | $mg\ L^{-1}$ | 164 ± 5 | 141 ± 2 | 122 ± 3 | 140 ± 3 | 139 ± 4 |
| | % removed | | 14.0% | 25.4% | 14.5% | 14.5% |
| Turbidity after 30 m | NTU | 3100 ± 71 | 52 ± 6 | 54 ± 2 | 401 ± 15 | 40 ± 2 |
| | % removed | | 98.2% | 98.2% | 87.4% | 98.7% |
| Turbidity after 3 h | NTU | | 12 ± 1 | 18 ± 1 | 48 ± 3 | 10 ± 3 |
| | % removed | | 99.6% | 99.4% | 98.5% | 99.7% |

As can be seen from Table 12, addition of NC24 or NH19 nanocomposites removed turbidity almost completely after 3 h. For NC24 the removal was faster and already after 30 m complete clarification was observed. FIGS. 20A-20B are pictures of cowshed effluents taken 10 min or 60 min, respectively, after addition of NC24 alone or with the bridging agent. It should be emphasized that when the bridging agent is added the clarification was quick (a matter of seconds), and the thickness of the sludge was considerably lower.

With respect to the chitosan nanocomposites (NH19) it can be seen from Table 12 that they were not effective in removing COD, whereas NC24 removed about 56% when added alone and the removal of COD was improved even more when NC24+BP. A similar behavior of improved removal with BP was observed for total N with NC24, whereas in NH19 no influence of BP can be seen.

A somehow puzzling difference between nanocomposites was observed for Cl: whereas NC24 alone increased its concentration, an addition of BP reduced chlorine to values lower than in the raw effluents. We assume that CF ions bind to the flocks, and BP enhances such a binding. NH nanocomposites behave differently: it seems that the chitosan itself binds Cl⁻ ions, whereas an addition of BP handicaps such a binding.

13.3 Pretreatment of Cowshed Effluent with New Nanocomposites with or without a Bridging Agent (BP)

As a next step, nanocomposites suspensions with 1% clay and with a load of 1 g polymer per g clay were prepared for more than 10 cationic and anionic polymers. Charges for the different nanocomposites were measured and ranged from −70 to +110 $mole_c\ L^{-1}$. Due to the need to neutralize the negative charge of cowshed effluents, only three new nanocomposites with the highest positive charge were chosen. Thus, nanocomposites were prepared from poly(dimethylamine-co-epichlorohydrin-co-ethylenediamine) (PDEE); poly[bis(2-chloroethyl) ether-alt-1,3-bis[3-(dimethylamino)-propyl]urea] quaternized (PQ2); or poly[(3-methyl-1-vinylimidazolium chloride)-co-(1-vinylpyrrolidone)], (PMVV).

For easier and more fluid suspensions nanocomposites were prepared as 1% sepiolite suspensions with polymer:clay ratios of 2:1, 1.5:1 and 1:1. The nanocomposite suspensions with approximately similar charge were tested for cowshed effluents clarification. Results are presented Table 13 below.

TABLE 13

Cowshed effluents treated with nanocomposites based on PMVV, PDEE or PQ2 polymers and 1% sepiolite, herein identified as LQ25, PM23 and P2-25, respectively

| Parameter | Units | Raw | LQ25 1% 2 g/g | PM23 1% 1.5 g/g | P2-25 1% 2 g/g |
|---|---|---|---|---|---|
| Polymer | | | PMVV | PDEE | PQ2 |
| Charge | $mole_c\ L^{-1}$ | −2.9 | 99.5 | 120.5 | 129.5 |
| Concentration needed for neutralization | $ml\ L^{-1}$ | | 29.1 | 24.1 | 22.4 |

TABLE 13-continued

Cowshed effluents treated with nanocomposites based on PMVV, PDEE or PQ2 polymers and 1% sepiolite, herein identified as LQ25, PM23 and P2-25, respectively

| Parameter | Units | Raw | LQ25 1% 2 g/g | | PM23 1% 1.5 g/g | | P2-25 1% 2 g/g | |
|---|---|---|---|---|---|---|---|---|
| Polymer | | | PMVV | | PDEE | | PQ2 | |
| | | | without BP | with BP | without BP | with BP | without BP | with BP |
| Added nano-composite | ml/L | | 30 | 24 | 25 | 21 | 23 | 18 |
| Added BP | ml/L | | | 20 | | 20 | | 20 |
| Cl | mg L$^{-1}$ | 2740 | 3220 | 1130 | 2950 | 1060 | 3340 | 2110 |
| COD | mg L$^{-1}$ | 5809 ± 205 | 2528 ± 418 | 2552 ± 315 | 2282 ± 101 | 2393 ± 293 | 3384 ± 366 | 3387 ± 43 |
| | % removed | | 56.49% | 56.08% | 60.72% | 58.81% | 41.75% | 41.70% |
| Total N | mg L$^{-1}$ | 164 ± 5 | 129 ± 2 | 122 ± 1 | 126 ± 2 | 123 ± 4 | 166 ± 5 | 150 ± 3 |
| | % removed | | 21.34% | 25.36% | 23.14% | 24.77% | −1.58% | 8.37% |
| Turbidity after 30 m | NTU | 3100 ± 71 | 53 ± 1 | 57 ± 2 | 61 ± 6 | 56 ± 4 | 52 ± 6 | 57 ± 2 |
| | % removed | | 97.60% | 97.55% | 98.05% | 98.21% | 98.32% | 98.16% |
| Turbidity after 3 h | NTU | | 5 ± 1 | 14 ± 1 | 26 ± 1 | 16 ± 3 | 14 ± 1 | 12 ± 1 |
| | % removed | | 99.85% | 99.58% | 99.15% | 99.50% | 99.54% | 99.62% |

In general the following observations can be made in view of the results presented in Table 13:

(a) As for clarification, all treatments were very effective after 3 h: remaining turbidity in all cases was less than 1%. As for the results after 30 m, the efficacy was also impressive. As mentioned above for NC24 and NH19 it should be emphasized that BP samples (i.e. nanocomposites with bridging agent (BP) clarified the effluent in seconds, and the thickness layer obtained was smaller.

(b) In contrast to the results with NC and NH nanocomposites (Example 13.2 above), addition of BP to LQ25, PM23 or P2-25 nanocomposites did not improve a COD removal. There was a slight difference in the performance of the three nanocomposites, when used alone. PM23 nanocomposites when used without addition of BP exhibited the best COD removal (about 60%). PQ2 exhibited the poorest performance (about 40%), but still was considerably better than NH19.

(c) A similar pattern was observed for removal of total N: as not as in NC, addition of BP did not improve nitrogen removal. The removal by PDEE and PMVV based nanocomposites (PM23 and LQ25, respectively) was similar to the values obtained by NC+BP, whereas PQ2 based nanocomposites (P2-25) apparently did not remove nitrogen at all.

(d) As for Cl removal—the pattern for all three nanocomposites was similar to the observed for NC: an addition of BP lowered the Cl concentration. In PDEE and PMVV based nanocomposites the reduction was even more significant leaving only about 35% of the initial Cl concentration.

To summarize the performance of the new nanocomposites, all three polymers offer very good clarification, and the addition of the bridging agent speeded up the process and increased the Cl removal. PDEE and PMVV based nanocomposites showed very effective COD and total N removal.

13.4 Pretreatment of Cowshed Effluent with Nanocomposites Consisting of Anchoring Particles and Low Charge Density Cationic Polyelectrolyte In the present example two additional aspects were tested (a) the use of a polyelectrolyte polymer with low charge density for the preparation of nanocomposites, i.e., nanocomposites consisting of anchoring particles and polyelectrolyte polymer with low charge density, and (b) a combination of two nanocomposites, in which the nanocomposites of (a) are added as a "bridging agent".

For the purpose of these experiment nanocomposites (denoted as NZ22) were prepared using sepiolite and 1 g of an acrylamide/dimethylaminoethylacrylate methyl chloride copolymer (AM-co-DMAEA), which can be also used as a bridging agent by itself. The result was a 1% nanocomposite suspension with a relative low charge. Table 14 shows results of cowshed effluents treated with 1% NZ22 only, and with a combination of NC24 and NZ22 in which NZ22 acts as a "bridging agent".

TABLE 14

Cowshed effluents treated with NZ22 or with NC24 + NZ22

| Parameter | Units | Raw | NZ22 | |
|---|---|---|---|---|
| Polymer | | | AM-co-DMAEA | |
| Charge | mole$_c$ L$^{-1}$ | −2.9 | 33.6 | |
| Concentration needed for neutralization | ml L$^{-1}$ | | 86.3 | |
| | | | alone | added as a "bridging agent" after NC24 |
| Added NZ22 1% | ml/L | | 90 | 20 |
| Added NC24 1% | ml/L | | | 20 |
| Cl | mg L$^{-1}$ | 2740 | 3470.0 | 2350 |
| COD | mg L$^{-1}$ | 5809 ± 205 | 2570 ± 165 | 2402 ± 71 |
| | % removed | | 55.75% | 58.65% |
| Total N | mg L$^{-1}$ | 164 ± 5 | 126 ± 3 | 122 ± 4 |
| | % removed | | 22.94% | 25.18% |
| Turbidity after 30 m | NTU | 3100 ± 71 | 61 ± 2 | 86 ± 15 |
| | % removed | | 98.00% | 97.20% |
| Turbidity after 3 h | NTU | | 41 ± 2 | 42 ± 3 |
| | % removed | | 98.70% | 98.70% |

As can be seen from Table 14, in all aspects, the combination of NC24 with NZ22 behaved similarly to NC24 with BP (Table 12). One of the disadvantages of using NZ22 alone was the large amount of suspension needed due to the relatively low charge of NZ22. It should be mentioned that the polymer/clay ratio in this case cannot be increased since the viscosity of the suspension makes it already difficult to use. Thus, NZ22 alone will require large doses of coagulant making the treatment relatively expensive.

Figure 21A:
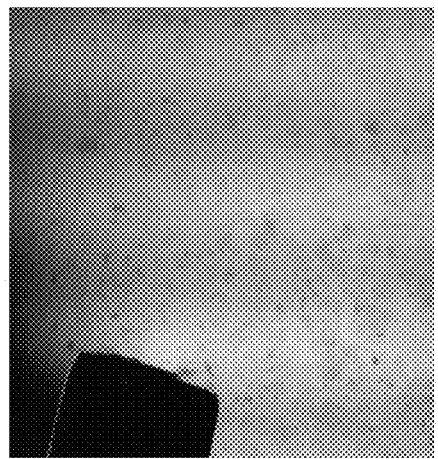
Figure 21B:
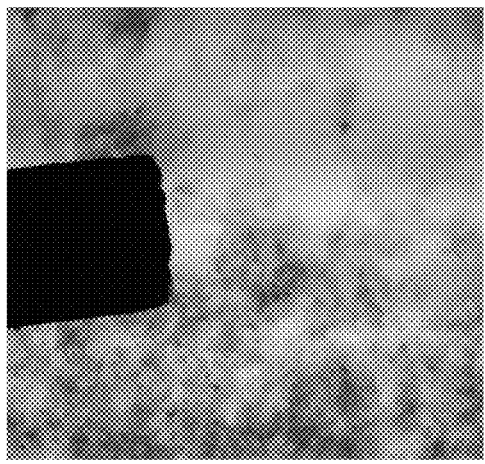
Figure 21C:
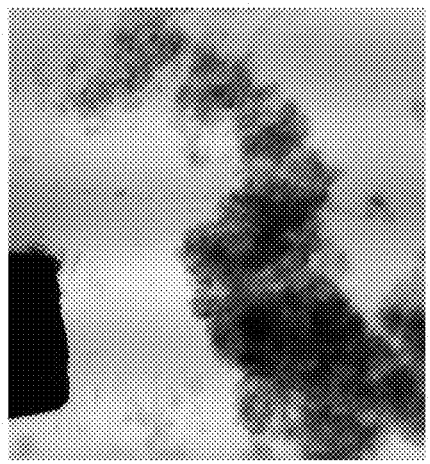
Figure 21D:
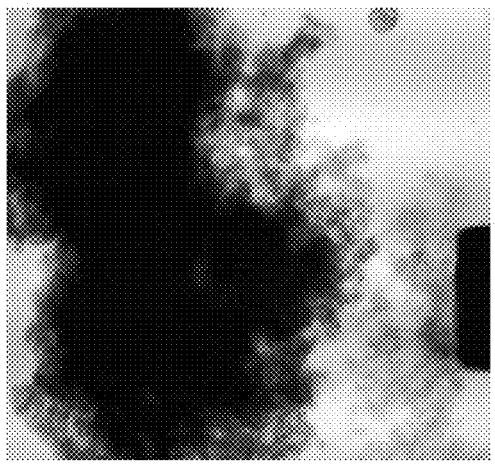

Combination of NC24+NZ22 appears to be a good treatment, even though clarification obtained was slightly lower than other treatments presented herein. FIGS. 21A-21D are pictures of a raw cowshed effluent (21A), of a cowshed effluent treated with NC24 (21B), with NC24 and BP (21C), or with NC24 and NZ22 (21D). In all pictures the black area represents a 400 µm thickness needle (introduced as a comparative length). As can be seen from FIG. 21D, the advantage of using both NC24 and NZ22 nanocomposites is the formation of very large flocks, even when compared with those obtained with the use of the bridging agent (FIG. 21C). Those large flocks are very stable and can easily undergo filtration. Thus, in cases where separation might be performed only by a filtration the use of two nanocomposites might deliver efficient colloids removal, while one is highly charged nanocomposite that neutralizes most of the effluents' colloidal charge, and the other nanocomposite with a lower charge allows formation of large aggregates.

REFERENCES

Copeland C., (2008), Animal Waste and Water Quality: EPA Regulation of Concentrated Animal Feeding Operations (CAFOs) (Congressional Research Service, November 17), http://www.nationalaglawcenter.org/assets/crs/RL31851.pdf.

Demirel B., Yenigun O., and Onay T T., (2005). Anaerobic treatment of dairy wastewaters: a review. Process Biochem. 40, 2583-2595.

Dipu, S., Anju, A., Kumar, V., and Thanga, S. G., (2010). Phytoremediation of dairy effluent by constructed wetland technology using wetland macrophytes. Global Journal of Environmental Research, 4, 90-100.

Dultz, S. and Rytwo, G., (2005) Effects of different organic cations on the electrokinetic surface charge from organo-montmorillonites—consequences for the adsorption properties. "Clays of Geotechnical and Economical Interest." Swiss, Austrian and German Clay Group—DTTG Annual Meeting. Celle, Germany, Oct. 5th-8th, 2005, DTTG Reports 11, 6-14.

Gonen and Rytwo, (2006). Using the dual-mode model to describe adsorption of organic pollutants onto an organoclay. J Colloid Interface Sci. 299(1):95-101.

Israeli Ministry of Environmental Protection. (2005), Inbar's Standards for Waste-water Quality, http://www.sviva.gov.il/Enviroment/Static/Binaries/Articals/tavla_inbar_1.pdf revisited Aug. 30, 2011 (in Hebrew).

Ruiz-Hitzky, E. (2001). Molecular access to intracrystalline tunnels of sepiolite, J. Mater. Chem. 11: 86-91.

Rytwo, G., (2012). The use of clay-polymer nanocomposites in wastewater pretreatment. The Scientific World Journal, 2012, Article ID 498503, 7 pages. doi:10.1100/2012/498503.

Rytwo, G. and Gonen, Y. (2006). Very fast sorbent for organic dyes and pollutants. Colloid and Polymer Science, 284: 817-820.

Rytwo, G. Kohavi, Y. Botnick, I. and Gonen, Y. (2007). Use of CV- and TPP-motmorillonite for the removal of priority pollutants from water. Applied Clay Science, 36: 182-190.

Rytwo, G. Rettig, A. and Gonen, Y. (2011). Organo-sepiolite particles for efficient pretreatment of organic wastewater: application to winery effluents. Applied Clay Sciences, 51: 390-394.

Rytwo, G., Lavi, R., and König, T. N., (2012) Influence of Freezing OMW on its pretreatment. Olive Oil Wastes and Environmental Protection Symposium, Chania Greece, 2012.

Rytwo, G., Lavi, R., Rytwo, Y., Monchase, H., Dultz, S., König, T. N., (2013). Clarification of olive mill and winery wastewater by means of clay polymer nanocomposites. Science of the Total Environment, 442, 134-142.

Salopek, B., Krasić, D., Filipović, S. (1992). Measurement and application of zeta-potential, Rudarsko-Geološko-Naftni Zbornik (ISSN 0353-4529), Vol. 4: 147-151.

von Homeyer, A., D. Krentz, W. Kulicke and D. Lerche. (1999) Optimization of the polyelectrolyte dosage for dewatering sewage sludge suspensions by means of a new centrifugation analyser with an optoelectronic sensor. Colloid & Polymer Science 277:637-645.

The invention claimed is:

1. A method for pretreatment of wastewater for reduction of total suspended solids (TSS) and turbidity, wherein the wastewater is from olive oil mills, wineries, piggeries, cowsheds, slaughterhouses, fruit and vegetable processing industries, soy or coffee bean industries, bromine industries, dairy effluents, or saline effluents, and includes charged colloidal particles suspended therein, said method consisting of treating the wastewater with: (a) a nanocomposite and (b) a bridging agent, the nanocomposite (a) consisting of:

(ai) anchoring particles based on zeolites, diatomaceous earth, powdered activated carbon or aluminium or magnesium silicate clay minerals selected from the group consisting of sepiolite, palygorskite, smectite, montmorillonite, vermiculite, hectorite, laponite, bentonite, or saponite, and (aii) one or more polymers, at least one of said polymers being a cationic polyelectrolyte polymer selected from the group consisting of: poly(diallyl dimethylammonium) chloride (poly-DADMAC), cationic polyacrylamide, poly(dimethylamine-co-epichlorohydrin-co-ethylenediamine) (PDEE), poly[bis(2-chloroethyl) ether-alt-1,3-bis[3-(dimethylamino)propyl]urea] quaternized (PQ2), poly [(3-methyl-1-vinylimidazolium chloride)-co-(1-vinylpyrrolidone)] (PMVV), chitosan, poly [(2-ethyldimethylammonioethyl methacrylate ethyl sulfate)-co-(1-vinylpyrrolidone)], quaternized hydroxyethylcellulose ethoxylate, and guar gum, or an anionic polyelectrolyte polymer selected from the group consisting of: a poly(methyl vinyl ether-alt-maleic anhydride) copolymer (PMVE) and a poly(acrylamide-co-acrylic acid) copolymer (PAM); and the bridging agent (b) is selected from the group consisting of:

(bi) a cationic polyelectrolyte polymer selected from the group consisting of: polyquaternium 2 (PQ2), polyquaternium 15 (PQ15), polyquaternium 45 (PQ45), and polyquaternium 47 (PQ47);

(bii) an anionic polyelectrolyte polymer selected from the group consisting of poly(acrylamide-co-acrylic acid), acrylamide/sodium acryloyldimethyltaurate copolymer, and acrylamide/sodium acryloyldimethyltaurate/ acrylic acid terpolymer; or (biii) a nanocomposite consisting of anchoring particles as defined above in (ai) and a cationic polyelectrolyte polymer as defined above in (bi) or an anionic polyelectrolyte polymer as defined above in (bii), whereby said polyelectrolyte polymer (aii) of the nanocomposite (a) neutralizes the charged colloidal particles suspended in said wastewater while anchoring them to the anchoring particles (ai) of the nanocomposite to form small flocks of about 50 to 100 µm in size and said bridging agent (b) completes the neutralization and bridges the small flocks to form large aggregates of about 200 to 2000 µm in size, thus enhancing their precipitation and achieving a reduction of TSS and turbidity of two orders of magnitude in a time range of less than 5 minutes.

2. The method according to claim 1, wherein the anchoring particles are based on clay minerals selected from the group consisting of sepiolite, palygorskite, smectite, montmorillonite, vermiculite, hectorite, laponite, bentonite, and saponite.

3. The method according to claim 2, wherein the clay mineral is sepiolite or bentonite.

4. The method according to claim 1, wherein the nanocomposite consists of anchoring particles and one, two or three polymers, at least one of which is a cationic or anionic polyelectrolyte polymer.

5. The method according to claim 4, wherein the nanocomposite consists of anchoring particles and one polymer, which is a cationic or an anionic polyelectrolyte polymer.

6. The method according to claim 5, wherein the cationic polyelectrolyte polymer is poly-DADMAC, PDEE, PQ2 or PMVV chitosan.

7. The method according to claim 1, wherein said nanocomposite is selected from the group consisting of poly-DADMAC-sepiolite, poly-DADMAC-bentonite, chitosan-sepiolite, PDEE-sepiolite, PQ2-sepiolite, PMVV-sepiolite, PMVE-sepiolite, and PAM-sepiolite.

8. The method according to claim 1, wherein the bridging agent is a cationic polyelectrolyte polymer selected from the group consisting of polyquaternium 15 (PQ15), polyquaternium 45 (PQ45), and polyquaternium 47 (PQ47).

9. The method according to claim 1, wherein the bridging agent is a nanocomposite consisting of anchoring particles and a cationic or an anionic polyelectrolyte polymer.

10. The method according to claim 9, wherein the bridging agent is the nanocomposite PQ15-sepiolite, PQ45-sepiolite, or PQ47-sepiolite.

11. The method according to claim 1, wherein the wastewater contains negatively charged colloidal particles, the nanocomposite consisting of anchoring particles and at least one cationic polyelectrolyte polymer is added thereto in an amount that causes partial neutralization of the negatively charged colloidal particles and a cationic polyelectrolyte polymer bridging agent is added either together with, or after, the addition of the nanocomposite, to complete the neutralization of the partially neutralized negatively charged colloidal particles while bridging the small flocks formed into large aggregates.

12. The method according to claim 11, wherein partial neutralization of the negatively charged colloidal particles by the nanocomposite with a cationic polyelectrolyte polymer is achieved by adding about 40% to about 90% of the charge needed to neutralize the negatively charged colloidal particles and the cationic polyelectrolyte polymer bridging agent completes the neutralization of the partially neutralized negatively charged colloidal particles while bridging the small flocks formed into large aggregates.

13. The method according to claim 1, wherein the wastewater contains negatively charged colloidal particles, the nanocomposite consisting of anchoring particles and at least one cationic polyelectrolyte polymer is added thereto with a total charge that is higher by about 10% than the charge of the negatively charged colloidal particles suspended in the wastewater, causing formation of positively charged small flocks, which are neutralized and caused to form large aggregates by later addition of an anionic polyelectrolyte polymer bridging agent.

14. The method according to claim 1, wherein the wastewater contains positively charged colloidal particles, the nanocomposite consisting of anchoring particles and at least one an anionic polyelectrolyte polymer is added thereto in an amount that causes partial neutralization of the positively charged colloidal particles and an anionic polyelectrolyte polymer bridging agent is added either together with, or after, the addition of the nanocomposite, to complete the neutralization of the partially neutralized positively charged colloidal particles while bridging the small flocks formed into large aggregates.

15. The method according to claim 1, wherein the wastewater contains positively charged colloidal particles, the nanocomposite consisting of anchoring particles and at least one an anionic polyelectrolyte polymer is added thereto with a total charge that is about 10% higher than the charge of the positively charged colloidal particles suspended in the wastewater causing formation of negatively charged small flocks, which are neutralized and caused to form large aggregates by later addition of a cationic polyelectrolyte polymer bridging agent.

16. The method according to claim 1, wherein the wastewater is from olive oil mills, cowsheds, bromine industries, or saline effluents.

* * * * *